(12) United States Patent
Manne

(10) Patent No.: US 6,712,753 B2
(45) Date of Patent: Mar. 30, 2004

(54) ELECTROMAGNETICALLY INDUCED ANESTHESIA AND SENSORY STIMULATION

(76) Inventor: Joseph Manne, 128 St. Marks Pl. - Apt. 4B, New York, NY (US) 10009

( * ) Notice: Subject to any disclaimer, the term of this patent is extended or adjusted under 35 U.S.C. 154(b) by 111 days.

(21) Appl. No.: 10/005,526

(22) Filed: Nov. 12, 2001

(65) Prior Publication Data

US 2002/0099256 A1 Jul. 25, 2002

Related U.S. Application Data

(60) Provisional application No. 60/248,319, filed on Nov. 14, 2000.

(51) Int. Cl.[7] ............................. A61N 2/00; A61N 1/08
(52) U.S. Cl. ............................................... 600/9; 607/45
(58) Field of Search ........................... 600/9–26, 382, 600/390; 607/45, 139

(56) References Cited

U.S. PATENT DOCUMENTS

| | | | |
|---|---|---|---|
| 4,315,503 A | | 2/1982 | Ryaby et al. |
| 4,889,526 A | | 12/1989 | Rauscher et al. |
| 5,047,005 A | * | 9/1991 | Cadwell ........................ 600/13 |
| 5,116,304 A | * | 5/1992 | Cadwell ........................ 600/13 |
| 5,169,380 A | * | 12/1992 | Brennan ........................ 600/26 |
| 5,441,495 A | * | 8/1995 | Liboff et al. ..................... 600/9 |
| 6,042,531 A | * | 3/2000 | Holcomb ........................ 600/13 |
| 6,280,376 B1 | * | 8/2001 | Holcomb ........................ 600/13 |
| 6,402,678 B1 | * | 6/2002 | Fischell et al. ................. 600/13 |

FOREIGN PATENT DOCUMENTS

| WO | WO 200209811 A1 | * | 2/2002 | ............ A61N/2/02 |
|---|---|---|---|---|

* cited by examiner

*Primary Examiner*—Eric F. Winakur
*Assistant Examiner*—Nikita R Veniaminov

(57) ABSTRACT

Sensory stimulation and sensory anesthesia are induced by means of a device which creates a time varying magnetic field which, in turn, creates an electric field in a direction parallel to the nerve and at the nerve so as to cause either depolarization leading to an action potential and subsequent sensory stimulation or hyperpolarization and subsequent blockade of nerve impulses which causes sensory anesthesia.

12 Claims, 25 Drawing Sheets

```
function y=efld5(sy,sx,sz,rc,tm,vo,cp,ll,rs)
%EFLD5 calculates summed electric field and transmembrane potential
%rc is the radius of the coil
%rw is the radius of the wire (mm)
%rs is the resistance of the wire
%n is number of turns of the wire
%uo is magnetic permeability
%cp is the capacitance
%ds is the increment along the y axis
%vo is the initial voltage across capacitor
%cp is the capcitance of the coil circuit ;
rw = 0.1;
n  = 35;
%calculate current term
%inductance
mu = 1.256e-008;
%n is the number of turns in the wire coil
%n =(ll/(mu*rc*((log((8*rc)/rw))-1.75)))^0.5;

%ll = mu*rc*(n^2)*((log((8*rc)/rw))-1.75);
%ll=100e-006
%ga is axoplasmic conductance
% d is diameter of axon
d=0.0045;
rho=54.7;
L= 100*d;
ds=0.25;
ga=pi*(d^2)/(4*rho*L);
%gm  is nodal conductance
l=0.00015;
ggm = 0.128;
gm=pi*d*(l*ggm)
ra=gm/ga
wa=(rs/(2*ll))
lc = (1/(ll*cp));
wb=((lc-(wa^2))^0.5)
ds=L+1;
```

| 3a |
|---|
| 3b |
| 3c |
| 3d |
| 3e |
| 3f |

```
for i=1:200;
   %tt is the actual time
     tt= i * 0.00001;
   %dd= vo*cp*wb*exp(-wa*tt)*(((wa/wb)^2)+1);
dl=(rs/2)*((cp/ll)^0.5);
wn=(1/(ll*cp))^0.5;
wd=wn*((1-dl^2)^0.5);
trg =((wd*cos(wd*tt))-(dl*wn*sin(wd*tt)));
%the current
ci(i)=(vo/(wd*ll))*(exp(-dl*wn*tt))*sin(wd*tt);
%derivative of the current
di(i)=(vo/(wd*ll))*(exp(-dl*wn*tt))*trg;
end %dz is the increment in z
dz=-2 ;
%dx is the increment in x
dx= 0.2 ;
%dy is the increment in y
dy=0.5;
mu = 4*pi*1.0e-007;

z = sz;
for mm=1:3;
  z=z+dz
  x = sx;
%incrementing the x axis
for kk=1:40 ;
x = x+dx;
```

FIG. 3b

```
% incrementing the z axis

%the y axis
y=sy;
for ii=1:40;
y = y + dy;

rr = ((x^2)+(y^2)+(z^2))^0.5 ;
th = acos(z/rr);

if (y==0) & (x>0);
   ph=0;
   y=0.1;
elseif (y==0) & (x<0);
   ph=pi;
  y=0.1 ;
elseif (y~=0);
      ph = atan2(x,y) ;
   end kc = ((4*rc*rr*sin(th))/((rc^2)+(rr^2)+(2*rc*rr*sin(th))))^0.5;
[E,K] = ellipke(kc);
EE=E;
KK=K;
gg=(1/(kc^2))* (((2-kc^2)*KK)-(2*EE)) ;
if(abs(y) <= 1)
 gg=(pi*(kc)^2)/16;
end bb = 1/(((rc^2)+(rr^2)+(2*rc*rr*sin(th)))^0.5);
%ef is the electrical field
aa =(mu*rc*cos(ph))/pi;
eff(ii)= aa*bb*di(tm)*gg;
ya(kk,ii,mm)=eff(ii);
kcn(kk,ii,mm)=kc;
phi(kk,ii,mm)=ph;
end end
end
```

FIG. 3c

```
z=sz;
for mm=1:3;
  z=z+dz
  x = sx;
%incrementing the x axis
for kk=1:40;
x = x+dx;
% incrementing the z axis % nd is the number of nodes slong the axon
cds= dy/2;
nd=40;
%eff is the net field
cdy=dy/2;

%adding part of one field(J=1:20) to another
for j=1:nd;

eff(j)=ya(kk,j,mm);
end

% for j=1:nd;
  % if(kk<6)
  %  eff(j) = effya((kk+6),j,mm);
```

FIG. 3d

```
%   end
%   if((5<kk)&(kk<8));
%     eff(j)= ya((kk+6),j,mm) + ya((kk-5),j,mm);
%   end
%   if(kk>7)
  %   eff(j) = ya((kk-5),j,mm);
%   end
% end for j=1:nd;
  yya(kk,j,mm) = eff(j);
    end for j=1:nd
en(j)= (cdy*eff(j));
      end yz-en;
    nn=nd-1;
    enw=eye(nd);
    enw= -2*enw;

vec(1:nn)=1;
    tema=diag(vec,1);
    temb=diag(vec,-1);
    enw = enw + tema + temb;
    enw(1,1)--1;
    enw(1,2)= 0;
    enw(1,3)= 1;
    enw(nd,nd)=1;
    enw(nd,(nd-1))= -1;

vnw=eye(nd);
    ion=eye(nd);
    ion = (-ra)*ion;
```

FIG. 3e

```
       vnw =ion + tema + temb -(2*vnw);
       vnw(1,1)=1.42;
       vnw(1,2)=-1;
       vnw(nd,nd)= 0.58;
       vnw((nd),(nd-1))=1;
       ivv = inv(vnw);
       an = ivv*(enw*(en.'));
       an = an*1000,
       for zz=1:40;
abb(kk,zz,mm)=an(zz);
abe(kk,zz,mm)=eff(zz);

end end
end y=abb;
```

FIG. 3f

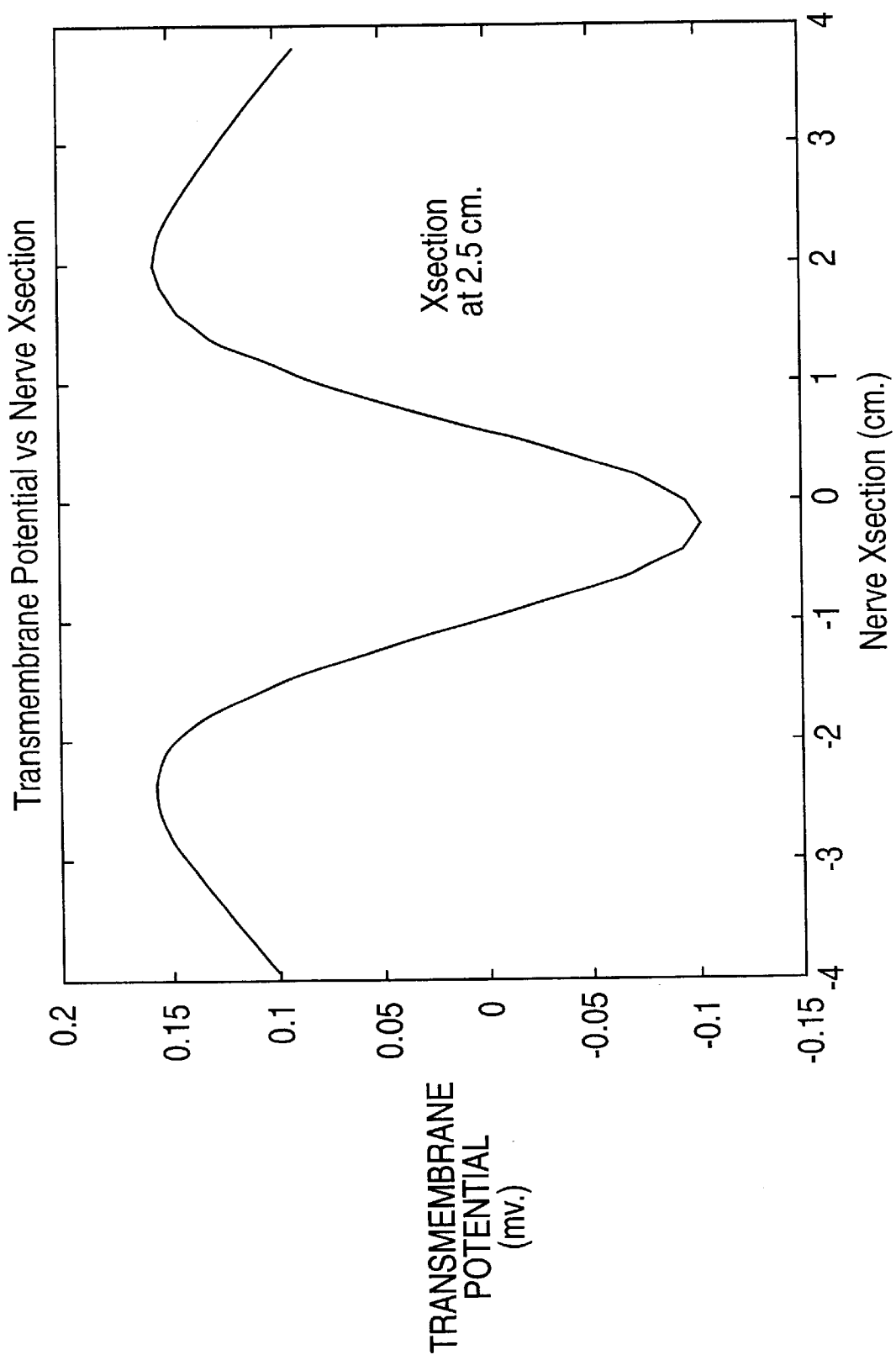

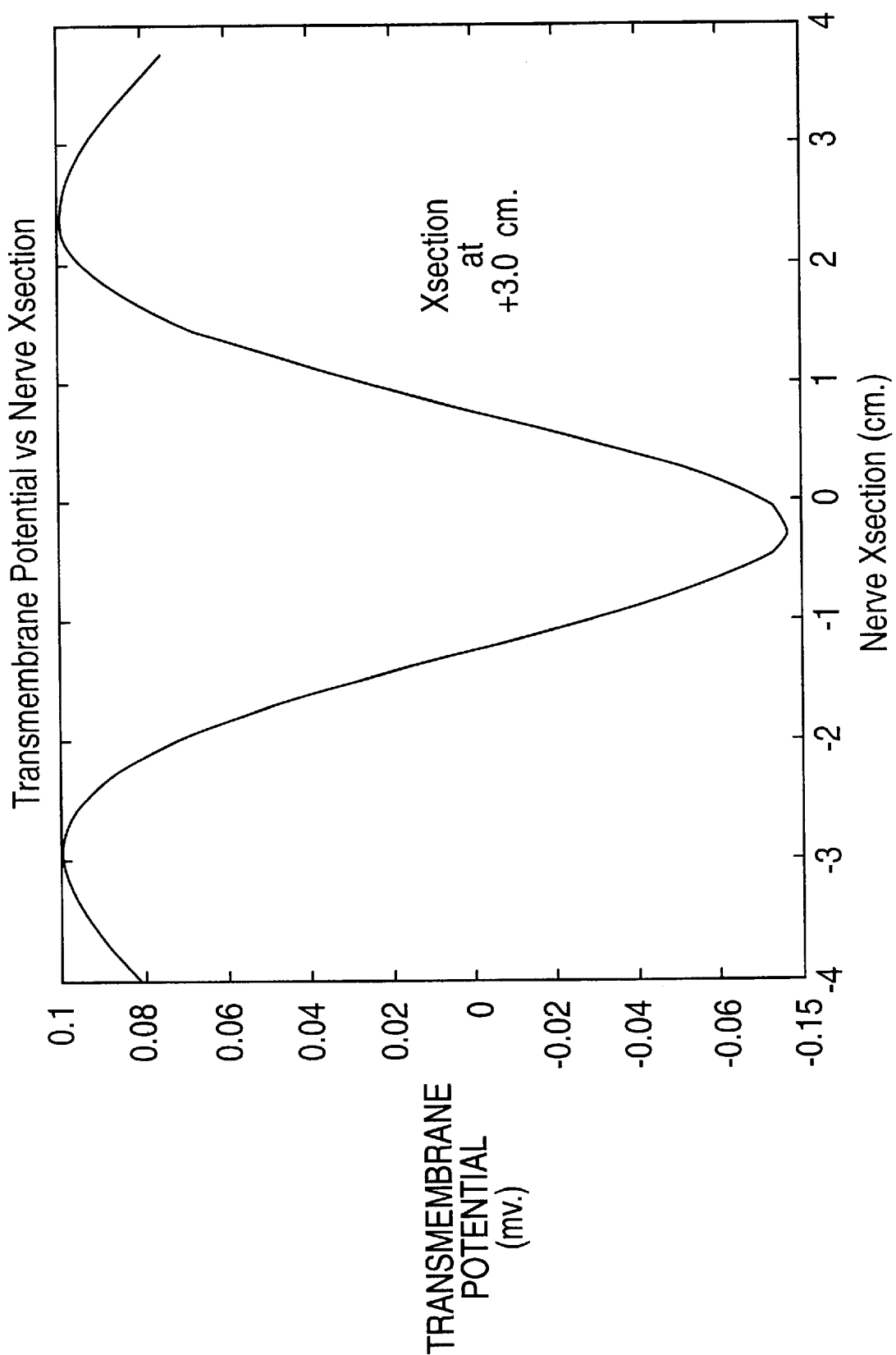

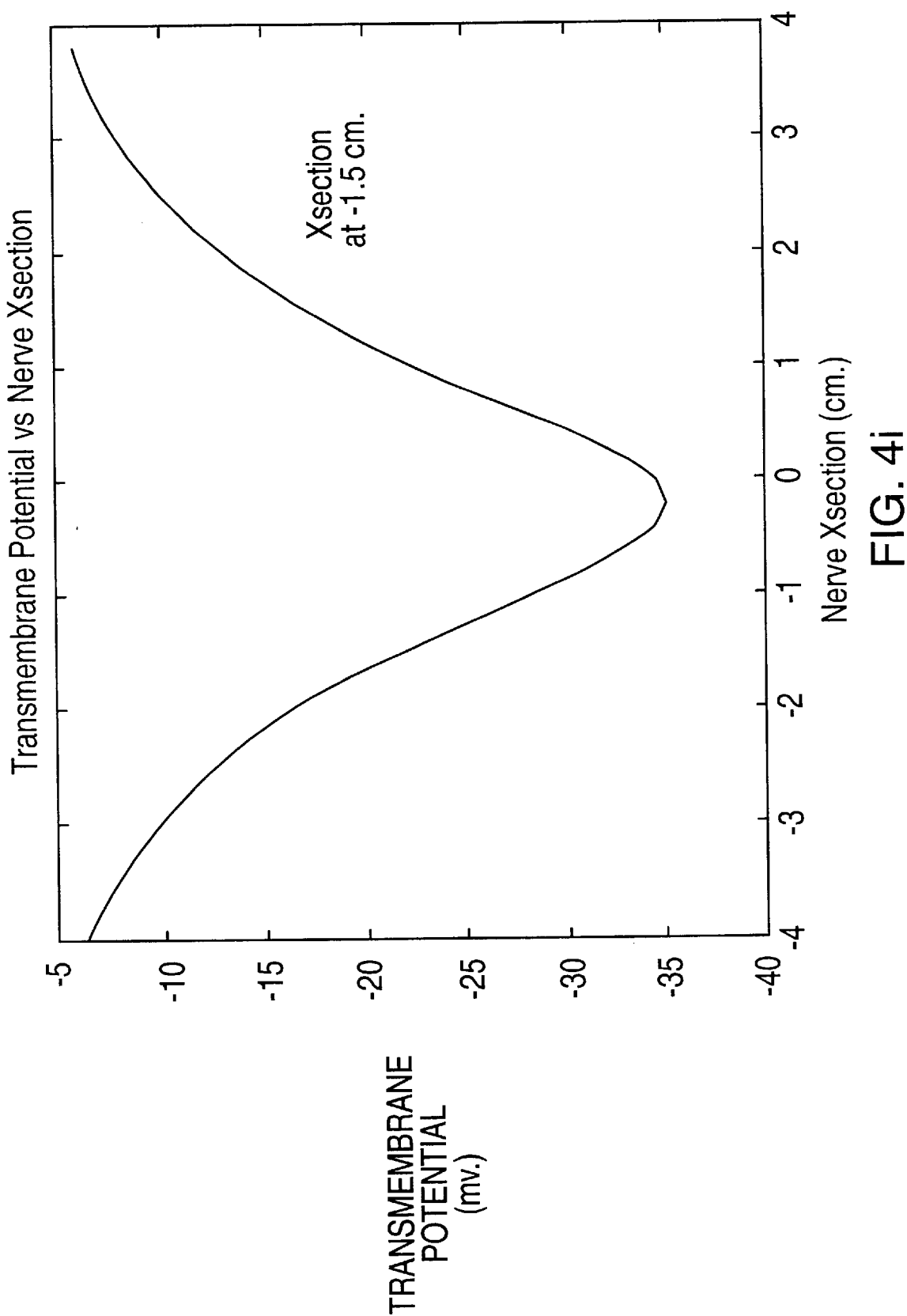

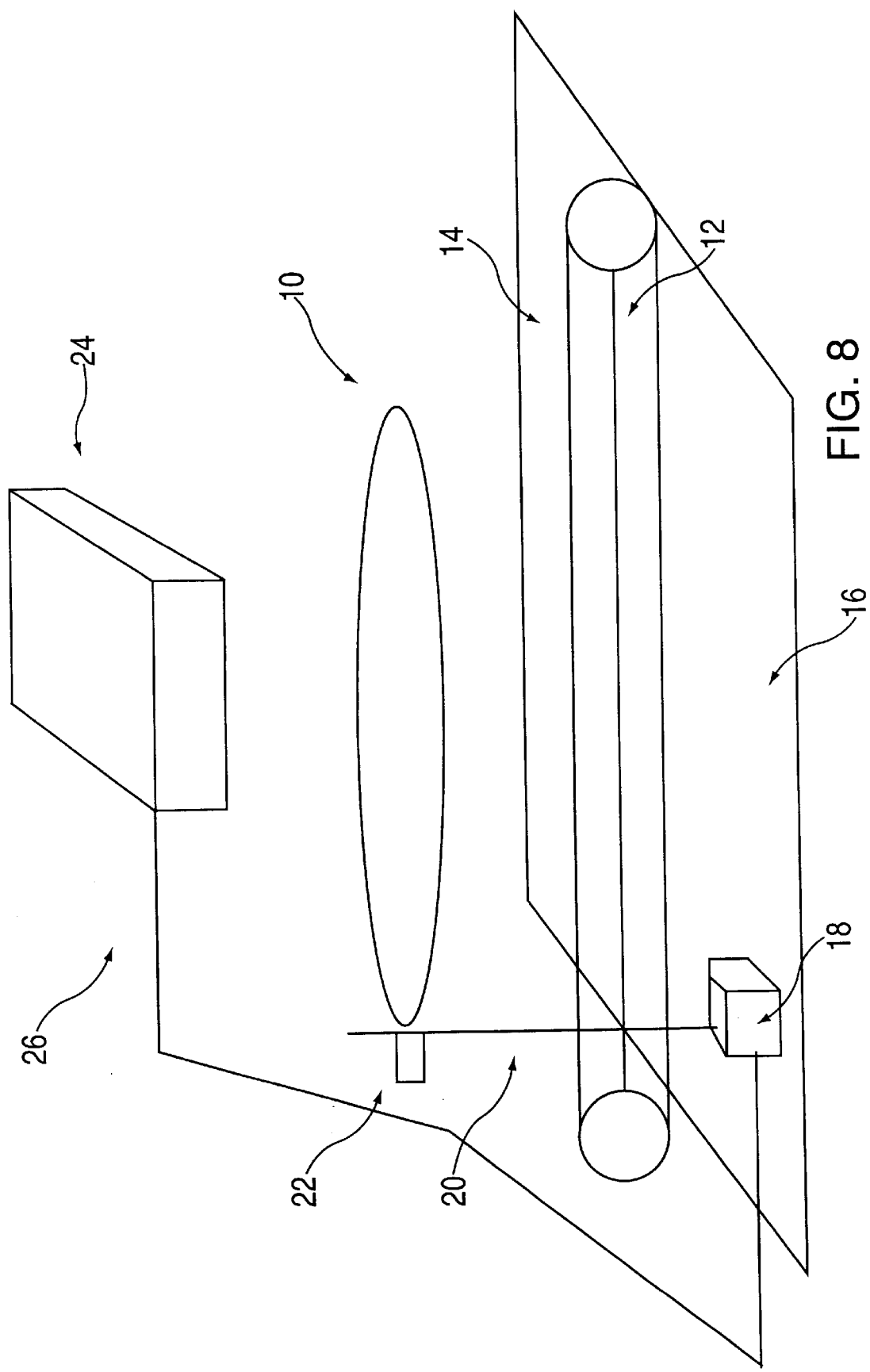

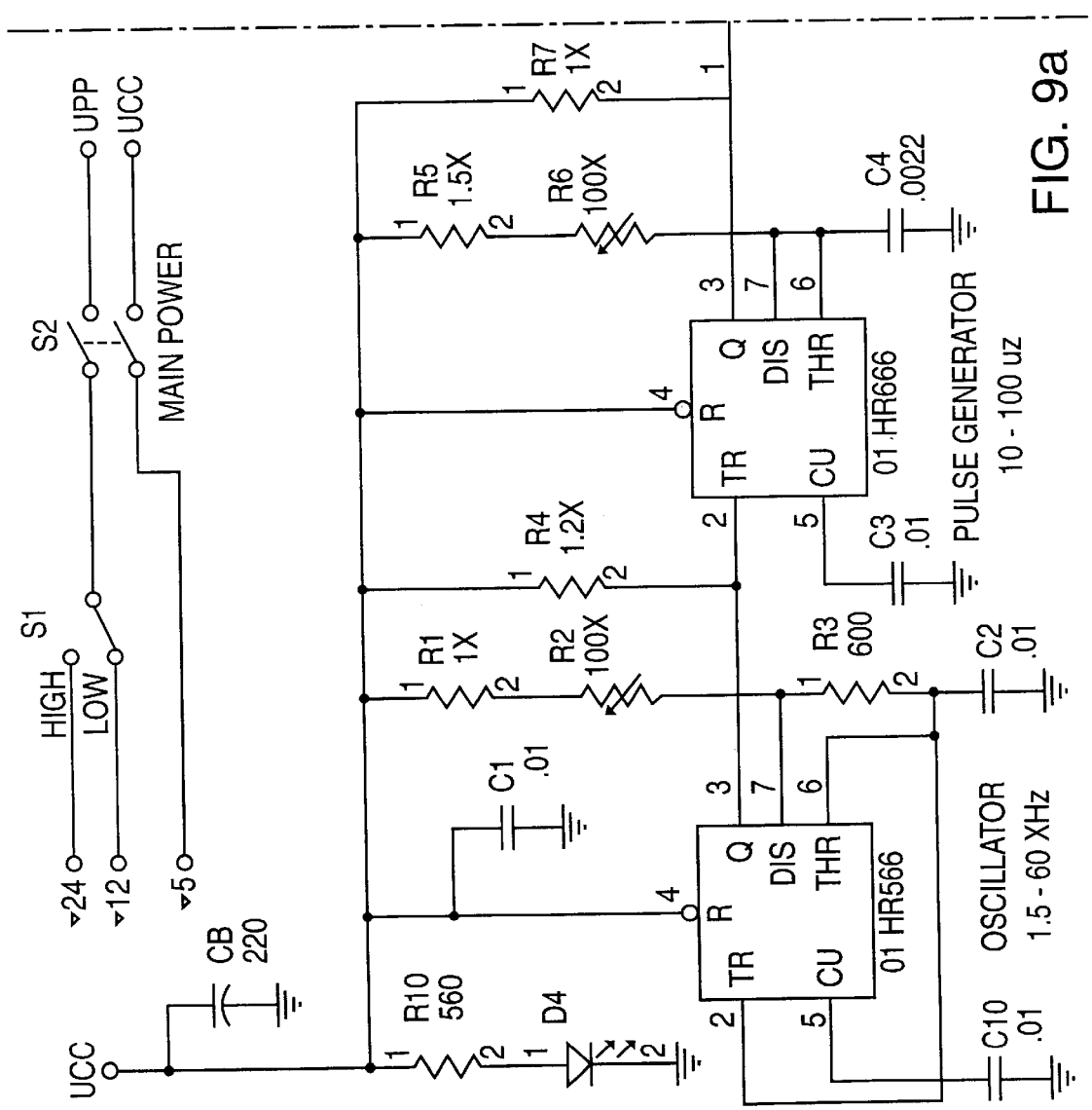

ELECTROMAGNETICALLY INDUCED ANESTHESIA AND SENSORY STIMULATION

This application claims the benefit of U.S. Provisional Application No. 60/248,319 filed Nov. 14, 2000.

BACKGROUND OF THE INVENTION

1. Field of the Invention

This invention relates to the production of sensory stimulation through the exposure of neural tissue to electromagnetic fields, and producing sensory anesthesia.

2. Description of the Prior Art

At the present time, all methods of sensory stimulation involve stimulation of the end organ. It will be understood that reference to sensory stimulation in this patent application refers to stimulation of the sensory nerves for the senses of smell, taste, and touch. For example olfactory stimulation, senses of smell, is achieved with the chemicals of scent. Perfume, air freshener scented soaps and candles are examples of the means by which a consumer experiences scent.

Nerve impulses are transmitted in the body by the nervous system which includes the brain, spinal cord, nerves, ganglia and the receptor. Nerves are made up of axons and cell bodies together with their respective protective and supporting structures. The axon is the long extension of the nerve cell that conducts nerve impulses to the next neuron.

The propagation of the nerve impulse along the axon is associated with an electric potential and a flow of cations into and out of the axon. This electric potential is called the action potential. The typical human action potential has an advancing front of depolarization with a peak value of +40 mV. In order to continue to propagate, the action potential must trigger the depolarization of the neural tissue directly at the front of the advancing wave.

In order to produce depolarization, the interior of the axon must be depolarized from its resting potential of −70 mV (a typical resting voltage potential) to a potential of −60 mV. However, once −60 mV is reached, the sodium channels in the axon opens and causes sodium cations (Na+) to flow into the axon, thereby allowing the depolarization to proceed to +40 mV. Other ion channels then open and cause the potassium cations in the axon to flow out of the axon until the interior of the cell repolarizes to −70 mV.

Thus, all that is necessary to propagate the action potential is to have an external potential which can bring the interior of the cell to −60 mV. Since the action potential consists of an advancing wave of +40 mV, under normal conditions the interior of the cell will depolarize to −30 mV (−70 mV+40 Mv) which is more than enough to propagate the action potential. As is known, these potentials are externally induced transmembrane potentials which are measured across the wall of the axon.

Given the fact that the nerve impulse is transmitted along the axon due to an electrical potential (the action potential), there have been a number of studies into the artificial propagation of nerve impulses using various electrical devices. For example, electrodes have been inserted into a nerve and a current passed through the nerve to cause movement of muscles.

Direct application of electric current has also been used to effect neurostimulation. In this technique, electrodes were applied directly to the skin or to underlying structures in a way which created an electric current between the two electrodes in the tissue in which the target neuronal structure was located. This technique employed a constant voltage source and was intended to cause neuronal transmission and thereby produce stimulation both in peripheral nerves and in the brain.

The influence of an external electric field on neuronal tissue has also been studied. One model for this is the effect of a monopolar electrode in the proximity of a neuron. (Rattay F, J Theor. Biol (1987) 125,339–349). The model for electrical conduction in the neuron which has been widely accepted is the modified cable equation:

$$\partial \frac{V}{\partial t} = \left[ \frac{d}{4\rho_i} \left( \partial \frac{V}{\partial x^2} + \partial \frac{V_e}{\partial x^2} \right) - i_i \right] / c_m \qquad \text{(eqn 1)}$$

where:

V represents voltage, $i_i$ is the total ionic current density, $\rho_i$=the resistivity of the axoplasm, $c_m$=capacitance of the membrane, Ve=externally applied voltage, the term:

$$\partial \frac{V_e}{\partial X^2} \qquad \text{(eqn 2)}$$

is referred to the activating function by Rattay because it is responsible for activating an axon by external electrodes.

The activating function has two possible effects on an axon. If its magnitude is sufficient there is a superthreshold response. This leads to the generation of an action potential. If this occurs then the cable equation will predict the expected response. In order to calculate the equation however the ionic current term $i_i$ must be calculated.

In order to calculate the ionic current, an equation of membrane ionic current, as a function of the externally induced transmembrane potential, is used. For myelinated membranes the Hodgkin-Huxley equation can be used. For unmyelinated membranes the Huxley-Frankenhaeuser equation is used.

There are other equations which account for membrane temperature as well. The other possible effect on the axon is subthreshold stimulation.

If a subthreshold stimulus is applied, then the transmembrane voltage is directly related to the activating function. The voltage changes due the opening of voltage sensitive ionic channels can be ignored. The calculation of transmembrane voltage becomes simplified. It is the subthreshold stimulation of the neuron which is considered in this patent application.

SUMMARY OF THE INVENTION

The present invention produces sensory stimulation by exposing a patient to different spatially and temporally varying electromagnetic fields by means of a magnetic flux generator positioned external to the patient. More specifically, the invention produces areas of depolarization which lead to the propagation of nerve signals. Thus, this invention provides for an entirely new form of sensory stimulation. In addition to sensory stimulation this invention provides a means to block retrograde neural conduction that arises when sensory stimulation is produced. This same method of neural blockade can be used on its own to produce sensory anesthesia.

The term "electromagnetic sensory stimulation" will be used to refer to stimulating nerves with a varying electromagnetic field using a magnetic flux generator positioned external to a body in this specification. It also produces areas of hyperpolarization which act to prevent the transmission of action potentials down axons surrounding the target axon. Thus the axonal stimulation can be focused by using a combination of depolarization and hyperpolarization.

This invention also provides a localizing system. In the prior art of neurostimulation, it is usually administered in a manual way in which the neurophysiologist places a needle in close proximity to the targeted nerve by direct hand manipulation. The needle is manipulated to the endpoint of eliciting paresthesia or by muscle twitch when using a neurostimulator.

However, with manual needle manipulation, it is difficult to guarantee smooth progression from one point to another. It is also difficult to ensure that all points within a certain region have been probed with the needle. The present invention avoids these problems.

Broadly, the method of the present invention is a method for sensory stimulation or sensory blockade in a patient comprising the steps of creating a time varying magnetic field with a device positioned completely external to said patient, said time varying magnetic field resulting in an electric field which creates one or more regions of hyperpolarization or depolarization along neural tissue, for as long as required, said regions of depolarization causing the propagation of a sensory neural impulse and said regions of hyperpolarization being of sufficient magnitude to block the propagation of nerve impulses in said neural tissue preventing retrograde sensory conduction or producing sensory anesthesia.

Preferably, the device is a coil which can produce a time varying magnetic field. Also, preferably, the device consists of a resistor, capacitor and inductor in series. The capacitor is discharged through the device so as to form a time varying magnetic field which in turn creates said electric field.

Preferably, the coil is circular in shape and has about 7 to about 10 turns, and the coil has a diameter of about 3 to about 7 cm.

Preferably, a time varying current passes through the device and the time varying current increases from 0 to about 6000 amps in 60 microseconds.

It is also preferred that the coil has a resistance (R) of about 0.1 to about 0.5 ohms and an inductance (L) of about 10 to about 90 microhenries.

The present invention also includes a system which consists of multiple devices as described above and each of the devices is configured so that the effect of the devices is to produce a continuous blockade of one or more nerves. It is also preferred that the system produces an electric field which creates a triphasic potential within the axon, said triphasic potential consisting of a virtual cathode surrounded by a virtual anode on each side of said virtual cathode.

The present invention also comprises a configuration consisting of multiples of the system which permit blockades of more than one neuron at the same time.

The system of the present invention preferably has coils of wire which are organized in such a way to allow production of a strong focused electric field at one or more interior points in the brain while sparing all other points in the brain.

Preferably, the coils are positioned with a three dimensional electromechanically controlled positioning system. It is also preferred that the coils are affixed to the body part containing a target nerve thus providing for continuous acute or chronic pain control.

The present invention can further be characterized as a method for producing sensory stimulation or sensory anesthesia in a patient by:

(1) creating a magnetic flux with a magnetic flux generator, said generator being positioned completely external to the patient and not in physical contact with the patient; and (2) treating a nerve of said patient with said magnetic flux to cause a depolarized region, a hyperpolarized region, or a combination of depolarized and hyperpolarized regions along an axon which leads to a focused propagation of an action potential in said nerve.

As is known, a time varying magnetic field, which is a magnetic flux, results in an electric field. The orientation and strength of the magnetic flux and its resulting electric field is such that it depolarizes, hyperpolarizes or both depolarizes and hyperpolarizes regions along the axon so as create areas of neurostimulation and regions of neuronal blockade( which prevents the propagation of the action potential).

To accomplish sensory stimulation in accordance with the present invention, a preliminary study is performed wherein the sensory nerve response to specific stimuli is recorded. More specific microelectrodes are used to measure the individual axonal response of a nerve to specific sensory stimuli. The axonal action potentials created by the magnetic flux reproduce the previously measured axonal responses to sensory stimuli thereby causing sensory perception. Those areas of hyperpolarization prevent the action potentials from traveling in the retrograde direction (opposite the normal direction of flow). These areas of blockade are used to cause sensory anesthesia or analgesia.

The strength of depolarization/hyperpolarization is expressed as a voltage and is a measurement of the voltage or electric potential between the inside of the axon and the outside of the axon. This electric potential is sometimes referred to as the externally induced transmembrane potential since it is measured across the cell wall.

For depolarization, the magnetic flux should be of such an orientation and strength so as to create a net externally induced transmembrane potential equal to or greater than −60 mV. More preferably, the electric potential created by the magnetic flux of the present invention should be about −50 mV or greater and, more preferred, about −40 mV or greater. It should be understood that "greater" means more positive.

For hyperpolarization, the magnetic flux should be of such an orientation and strength so as to create an electric potential of less than −100 mV. More preferably, the electric potential created by the magnetic flux should be about −110 mV or less, and, more preferably, about −120 mV or less. It should be understood that "less" means increasing in negativity.

The orientation of the electric field is such that it has a component parallel to the long axis of the axon. It is thought that the depolarization and/or hyperpolarization prevents the sodium and potassium gates from moving the cation across the cell membrane.

Preferably, the configuration of magnetic flux generators produces both a depolarized region and a hyperpolarized region adjacent to each other. This ensures only one way propagation of a nerve signal down an axon.

The magnetic flux generator of the present invention, consists of a RLC (resistor, inductor capacitor) circuit with a coil of wire as the inductor. The magnetic flux generates both a depolarized and hyperpolarized region. The externally induced transmembrane potentials for the combined depolarized and hyperpolarized regions have a strength and orientation as referred to above, e.g. depolarized equal to or greater than −60 mV, and hyperpolarized less than −100 mV.

Suitable magnetic flux generators which can be used in the present invention include any device which is capable of creating and projecting a magnetic flux. It is known that an antenna with associate circuitry can create and project magnetic fluxes. Additionally, a magnetron tube with associate circuitry is also capable of creating and projecting magnetic fluxes. Preferably, a circuit with an inductive element is used.

Suitable inductive elements include a coil of wire of various shapes and sized such as a round, figure eight, square, torroidal, etc. Most preferably, the magnetic flux generator is an RLC circuit with a round coil of wire. As will be appreciated by one of skill in the art, any high DC voltage pulsed power supply can be employed with the inductive elements.

The round coil of wire is preferably in series with a capacitor and a resistor so as to form a RLC circuit. The capacitor is discharged through the device so as to form a time varying magnetic field which in turn creates an electric field.

Additionally, two side-by-side magnetic flux generators can be used so as to create a distal hyperpolarized region and a proximal depolarized region. In order to create a unidirectional neural impulse the requisite axonal externally induced transmembrane potentials for these side by side magnetic field generators is the same as for the individual coil case. That is the depolarized region must be equal to or greater than −60 mV and the adjacent hyperpolarized regions are less than −100 mV.

Furthermore, a plurality of magnetic flux generators can be used such that no one individual magnetic flux generator produces the necessary electric field but that the combined generators, when oriented towards the same axon, produces a net electric field. That net electric field is of sufficient magnitude to produce a hyperpolarized and depolarized region of sufficient externally induced transmembrane potential to produce a unidirectional neural impulse. This technique of a focused array of coils would be used for dense neural tissue such as the spinal cord or brain where the field effects must be localized to a small region.

Another means of producing a focused electric field is to displace the magnetic coil so that only the relevant portion of the electric field is exposed to the nerve. This will also produce a focused externally induced transmembrane potential change. Putting two coils in the proper displaced orientation can produced two focused regions. One focused region of depolarization and one of hyperpolarization.

BRIEF DESCRIPTION OF THE DRAWINGS

These and other aspects of the present invention may be more fully understood by reference to one or more of the following drawings wherein:

FIG. 3 illustrates a computer program used to calculate externally induced transmembrane potentials;

FIGS. 4c–4g show the graphs of the externally induced transmembrane potential across different cross sections of the nerve bundle, corresponding to FIG. 4b;

FIGS. 4i–4k show the graphs of the externally induced transmembrane potential across different cross sections of the nerve bundle, corresponding to FIG. 4h;

FIG. 8 illustrates a positioning means for the coil of the present invention; and FIGS. 9a and 9b illustrate a schematic for a circuit that can deliver high frequency, high voltage DC current.

DETAILED DESCRIPTION OF THE INVENTION

Figure 1:
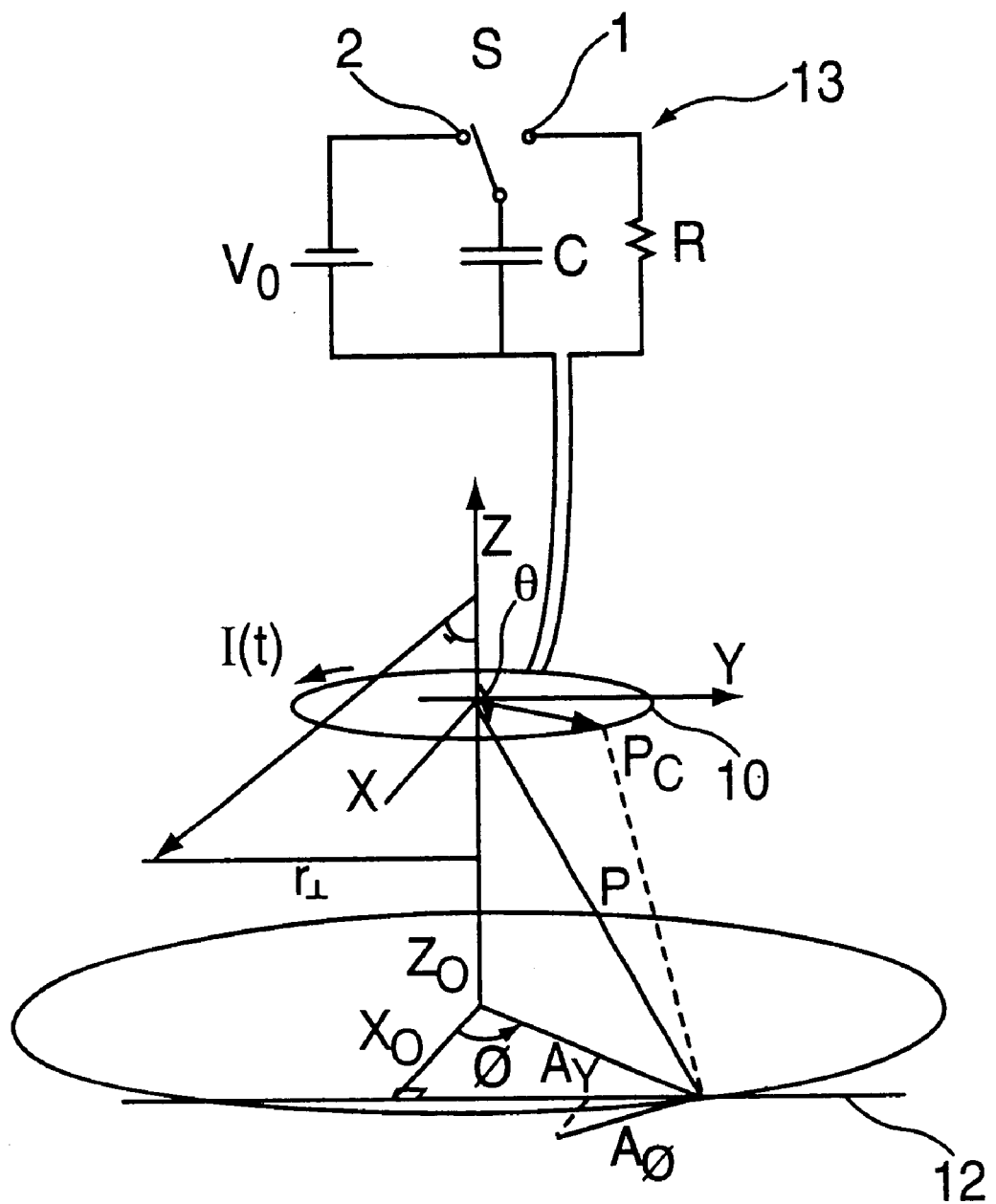
FIG. 1 is an overall schematic of the present invention illustrating the magnetic flux generator as a round coil in a RLC circuit.

FIG. 1 illustrates magnetic coil 10 overlying axon 12 and the coordinate system used to describe the three dimensional space around these elements. Coil 10 which lies above axon 12 consists of a series of turns of a conduction wire typically copper although other metals or alloys can be used. Coil 10 is the inductive component in the RLC circuit 13.

RLC circuit 13 is well known to those experienced in the art of electronics. It consists of resistor R, inductive element L, which is coil 10 in the circuit shown in FIG. 1, and capacitor C in series. The behavior of the RLC circuit 13 is well known to those experienced in the field of electronics. Voltage source Vo in conjunction with switch So is used to charge capacitor C when switch S is in position 1.

Capacitor C is then discharged through resistor R and coil 10 when switch S is moved to position 2. The total current I(+) and the rate of change of the current when capacitor C is discharged through resistor R and coil 10 can be calculated in a conventional manner.

Axon 12 is parallel to the y-axis; it lies Zo below the coil and Xo from its axis. When capacitor c is discharged, the current, I(t) in the coil induces an electric field in the tissue whose gradient in the direction of the nerve axis is the activating function. It determines the local transmembrane current in the axon and is related to the magnetic vector potential, Ao, and its component lying along the axon, Ay.

The externally induced transmembrane potential in axon 12 is calculated using the cable equation. The cable equation is:

$$\delta^2 \frac{\partial^2 V}{\partial x^2} - V - \alpha \frac{\partial V}{\partial t} = \delta^2 \frac{\partial E_x}{\partial x} \quad \text{(eqn 3)}$$

$$\frac{\partial E_x}{\partial x} \quad \text{(eqn 4)}$$

where

δ=space constant of the cable equation,

α=the time constant of the cable equation, the term: is referred to as the activating function. The activating function determines the transmembrane voltage for subthreadhold stimulation.

One of Maxwell's Equations relates the electric field E along the axon to the magnetic potential A created by the coil 10:

$$E = -\Delta\varphi - \frac{1}{c}\frac{\partial A}{\partial t} \qquad \text{(eqn 5)}$$

where the first term in the equation:

$$-\neq\Phi$$

represents the contribution to the electric field from fixed charge. In this particular example, there is no fixed charge contributing to the field thus this term can be eliminated and the equation for the electric field becomes:

$$E = -\frac{1}{c}\frac{\partial A}{\partial t} \qquad \text{(eqn 6)}$$

For the case of the coil with a time varying current, such as coil 10 in the present invention, the equation for the induced magnetic vector potential has been described (Jackson J D. Classical Electrodynamics. 1962, New York):

$$\frac{A}{c} = I(t)\frac{\rho_c \mu}{\pi}\int_0^2 \frac{\pi\cos\phi d\phi}{\sqrt{(\rho c)^2 + \rho^2 - 2\rho\rho_c \sin\theta\cos\phi}} \qquad \text{(eqn 7)}$$

the equation simplifies to:

$$\frac{A}{c} = \qquad \text{(eqn 8)}$$

$$I(t)\frac{\rho_c \mu}{\pi\sqrt{(\rho c)^2 + \rho^2 - 2\rho\rho_c \sin\theta\cos\phi}} x\left(\frac{2}{k^2}((K(k) - E(k)) - K(k))\right)$$

where k is defined by:

$$k^2 = \frac{4\rho_c\rho\sin\theta}{\rho_c^2 + \rho^2 - 2\rho\rho_c\sin\theta} \qquad \text{(eqn 9)}$$

substituting the expression for the magnetic vector potential into the expression for the component of the electric field along the axon 12 (y component):

$$E = \left(\frac{\partial A}{\partial t}\right) = \frac{d(I(t))}{dt}\frac{\rho_c\mu\cos(\phi)}{\pi\sqrt{(\rho c)^2 + \rho^2 - 2\rho\rho_c\sin\theta\cos\phi}} \times \qquad \text{(eqn 10)}$$

$$\left(\frac{2}{k^2}((K(k) - E(k)) - K(k))\right)$$

In order to calculate the value of the preceding equation, the time derivative of the current (dI/dt) must be determined. But to do this an expression for the current in the coil 10 must be obtained.

The circuit for the magnetic coil takes the form of an RLC circuit. There is a resistor R a capacitor C and the coil 10 which is the inductive element (L). The inductance of the coil can be calculated by standard formulas known to those experienced in the art (Smythe W R Static and Dynamic Electricity. New York: McGraw-Hill, 1968):

$$L = \mu_0 r_c N^2\left(\ln\left(8\frac{r_c}{r_w}\right) - 1.75\right) \qquad \text{(eqn 11)}$$

where

L is the inductance of the coil, rc is the coil radius, rw is the wire radius,

N is the number of turns in the coil, and mu is the magnetic permeability.

The equation for the current in an underdamped RLC circuit is also well known to those experienced in the art of electronics:

$$I(t) = \frac{V_o}{w_b L}e^{(-w_a\delta)t}\sin w_b t \qquad \text{(eqn 12)}$$

where $W_a=(1/LC)^{0.5}$ $W_b=W_a(1-\text{delta}^2)^{0.5}$ $\delta=R/2(C/L)^{0.5}$ Vo=initial voltage across capacitor, C is the capacitance of the capacitor (in farads), and R is the resistance of the resistor(in ohms).

The axial electric field gradient is the source term in the modified cable equation (Equation 1) for nerve conduction. The ultimate objective is to calculate the other variable in the equation which is the externally induced transmembrane potential, V in Equation 3.

Equation 3 is a nonlinear second order partial differential equation. Traditionally all equations in this class tend to be difficult to solve analytically. There have been many publications describing the solution of the modified cable equation (Nagarajan S S, Durand D M and Warman E N. Effects of Induced Electric Fields on Finite Neuronal Structures: A Simulation Study. Transactions on Biomedical Engineering 40(11), pgs; 1175–1187), 1993).

It has been a common practice to reduce the equation to a series of linear differential equations using a compartmental analysis technique. (Segev I Fleshman W and Burke R E, "Compartmental Models of Complex Neurons" Methods of Neuronal Modelling: From Synapses to Networks, Koch C and Segev I, Eds. Cambridge, Mass.; MIT Press, 1989, pgs: 63–97)

Figure 2:
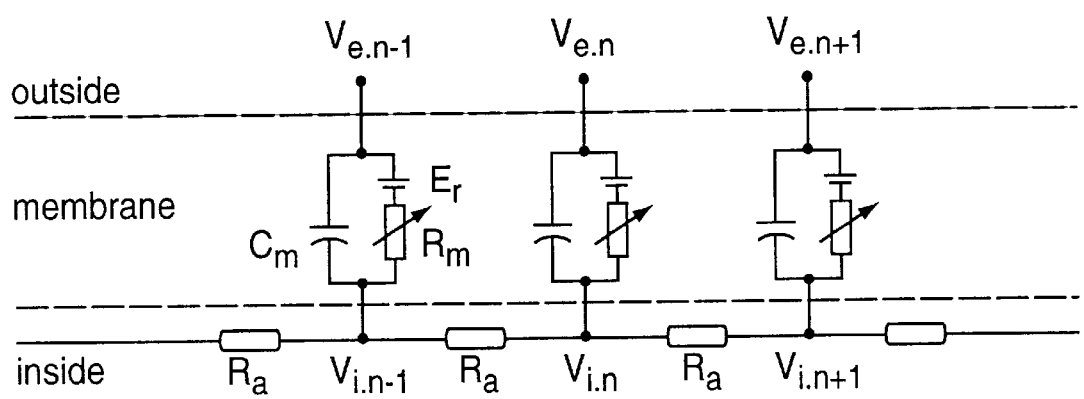
FIG. 2 illustrates a nerve modeled as a lumped circuit.

In this method the nerve is divided into N compartments. Each compartment is modeled as a lumped circuit. The repeating unit of this compartmental circuit is shown in FIG. 2. In the case of a myelinated nerve the repeating unit can be taken as the portion the nerve bounded by two adjacent nodes.

The axial current in each compartment is secondary to two factors. The first is the voltage gradient along the axon. The second is the extrinsically induced electric field from the externally fluxing magnetic field. The current can be related to these electric potential terms by Ohm's Law in the following fashion:

$$I = G(V_a - V_b) - G\int_a^b E_x dx \qquad \text{(eqn 13)}$$

where a and b are two adjacent nodes, $I_{net}$ is the axial current,

G is the conductance in the axon,

Ex is the axial component of the magnetically induced electric field, and

Va and Vb are the voltages at the two adjacent nodes.

In order to extend Equation 13 to the entire axon it is necessary to apply the above equation to a node and its two adjacent nodes such that a current balance equation for the central node is created, The equation for the transmembrane current at the middle node is:

$$I_{net}=G(V_c-2V_b+V_c)-G(\int_b{}^c(Ex)dx-\int_a{}^b(Ex)dx) \quad (eqn\ 14)$$

where the naming conventions used in Equation 13 apply and where Vb is the potential in the center node and Va and Vc are the potentials in the two surrounding nodes. The net transmembrane current can be expressed as the sum of channel current and the current due to the capacitative elements in the cell:

$$I_t = C\frac{dV}{dt} + I_i \quad (eqn\ 15)$$

where:

C dV/dt is the capacitative current term, and $I_{ch}$ is the ionic channel term.

This can be substituted into Equation 14 for the net current term Inet.

In the steady state condition the time dependent terms vanish and this equation now becomes:

$$I_{ch}=G(V_c-2V_b+V_c)-G(\int_b{}^c(Ex)dx-\int_a{}^b(Ex)dx) \quad (eqn\ 16)$$

Finally the transmembrane current through the center node in the subthreshold steady state $I_{ch}$ can be expressed as the product of the channel conductance Gm and the externally induced transmembrane potential Vb.

$$V_bG_M=G_a(V_c-2V_b+V_c)-G_a(\int_b{}^c(Ex)dx-\int_a{}^c(Ex)dx) \quad (eqn\ 17)$$

rearranging terms:

$$V_c - \left(\left(\frac{G_m}{G_a}+2\right)V_b\right) + V_a = \int_b^c (Ex)dx - \int_a^b (Ex)dx \quad (eqn\ 18)$$

Finally the equation is applied to all nodes such that each node is successively treated as the center node with the exception of the two terminal nodes:

$$V_{n+1} - \left(\left(\frac{G_m}{G_a}+2\right)V_n\right) + V_{n-1} = \int_{(n)dl}^{(n+1)dl} (Ex)dx - \int_{(n-1)dl}^{(n)dl} (Ex)dx \quad (eqn\ 19)$$

where:

n=2,3,4, . . . L−1, dl is he internodal distance, and

L is the total number of nodes in the nerve segment of interest.

For the two terminal nodes the applicable equations are:

$$for\ n=1 \quad \left(\left(\frac{G_m}{G_a}+1\right)V_1\right) - V_2 = \int_0^{2dl} (Ex)dx \quad (equ\ 20)$$

$$for\ n=L \quad V_n - \left(\left(\frac{G_m}{G_a}-1\right)V_{n+1}\right) = \int_{(L-1)dl}^{L(dl)} (Ex)dx \quad (eqn\ 21)$$

Thus, there are L equations in L unknowns. The unknowns are the externally induced transmembrane potentials located in the vector V=(V1, V2, V3, . . . Vl). The known quantities in the equations are the internodal potential differences due to the externally induced electric field: E={E1, E2, E3, E4 . . . EL). These are L linear simultaneous equations which can easily be solved by a variety of techniques.

A computer program, shown in FIG. 3, calculates the externally induced transmembrane potentials in the subthreshold condition. In this program the simultaneous equations are expressed as the matrix product of the matrix: A which contains the coefficients for V1, V2 . . . and the product of the matrix: B which contains the coefficients of E1, E2, E3 . . . leading to the following equation:

$$A*V=B*E \quad (eqn\ 22)$$

Then V can be solved for:

$$V=A^{-1}*B*E \quad (eqn\ 23)$$

Using the preceding equations it is possible to calculate the correct coil and circuit parameters to produce regions of depolarization and hyperpolarization along a nerve. Depolarization leads to a propagating neural impulse. The hyperpolarized areas can block the propagation of an action potential. This is desirable to prevent retrograde conduction.

Thus, a neural impulse can be propagated in a unidirectional fashion. The typical human action potential has an advancing front of depolarization with a peak value of 40 mv. In order to continue to propagate, the action potential must trigger the depolarization of the neural tissue directly at the front of the advancing wave.

In order to produce depolarization the interior of the axon must be depolarized from its resting potential of −70 mv to a potential of −60 mv. Once −60 mv is reached the sodium channels in the cell opens allowing the depolarization to proceed. Other ion channels can then open until the interior of the cell depolarizes to 40 mv.

Thus, all that is necessary to propagate the action potential is to have an external potential which can bring the interior of the cell to −60 mv. Since the action potential consists of an advancing wave of 40 mv, under normal conditions the interior of the cell will be depolarized to −30 mv which is more than enough to propagate the action potential.

In order to block the action potential, from propagating in the opposite direction, the interior of the cell must be sufficiently hyperpolarized so that the positive 40 mv depolarization cannot bring the cell to −60mv. This would mean the interior should be hyperpolarized to greater than −100 mv. Since the resting potential of the neuron is −70 mv, the additional transmembrane hyperpolarization produced by the external magnetic flux should be −30 mv or more, −40 mv is preferable to have a safe margin. This then would cause a nerve block.

Equations 12,13,20,21,22, and 23 can be used to calculate the resultant externally induced transmembrane potential induced for a specific set of coil and RLC circuit characteristics. Thus the circuit parameters required to produce +10 mv of depolarization or −30 mv or more of hyperpolarization at one or more points along an axon can be determined. This is the requirement for producing a unidirectional neural signal.

Equations 12,13,20,21,22, and 23 were incorporated into the computer program shown in FIG. 3. As described earlier, it calculates the externally induced transmembrane potential when the coil and circuit characteristics are provided. The input (independent variables) are coil radius, resistance capacitance, inductance and initial voltage for the RLC circuit, and the position of the coil with respect to the target axon.

As is understood by those skilled in the art, temperature can change the resting potential of the cell and, hence, can cause a change in the necessary electric field for propagation or blocking of the action potential. Additionally, other metabolic conditions can cause a change in the resting potential and, hence, would require a change in the necessary electric field generated by the magnetic flux in accordance with the present invention. Furthermore, it is known that some nerves have resting potentials which are greater than −70 mv. Again, adjustments are made to the magnitude of the magnetic flux so as to produce the necessary externally induced transmembrane potential.

EXAMPLE 1

This example illustrates sensing stimulation in accordance with the present invention.

Using this computer program it is thus possible to calculate the correct values for the RLC circuit and coil to produce sufficient transmembrane voltage to produce a unidirectional focused neural impulse. There are different possible combinations of circuit and coil parameters which will satisfy the required transmembrane voltage criteria. The following example illustrates one set of conditions which produces the desired effect. One set of values of circuit and coil which yield sufficient externally induced transmembrane potentials are:

Rc=radius of coil=1 cm,

Rw=radius of wire=1 mm,

Resistance R=0.21 ohms,

Capacitance C=0.0072 Farad,

Inductance of coil=L=9e-5 Henry,

Voltage=Vo=700 volts, and z0=height is coil above axon=3 cm.

Figure 4A:
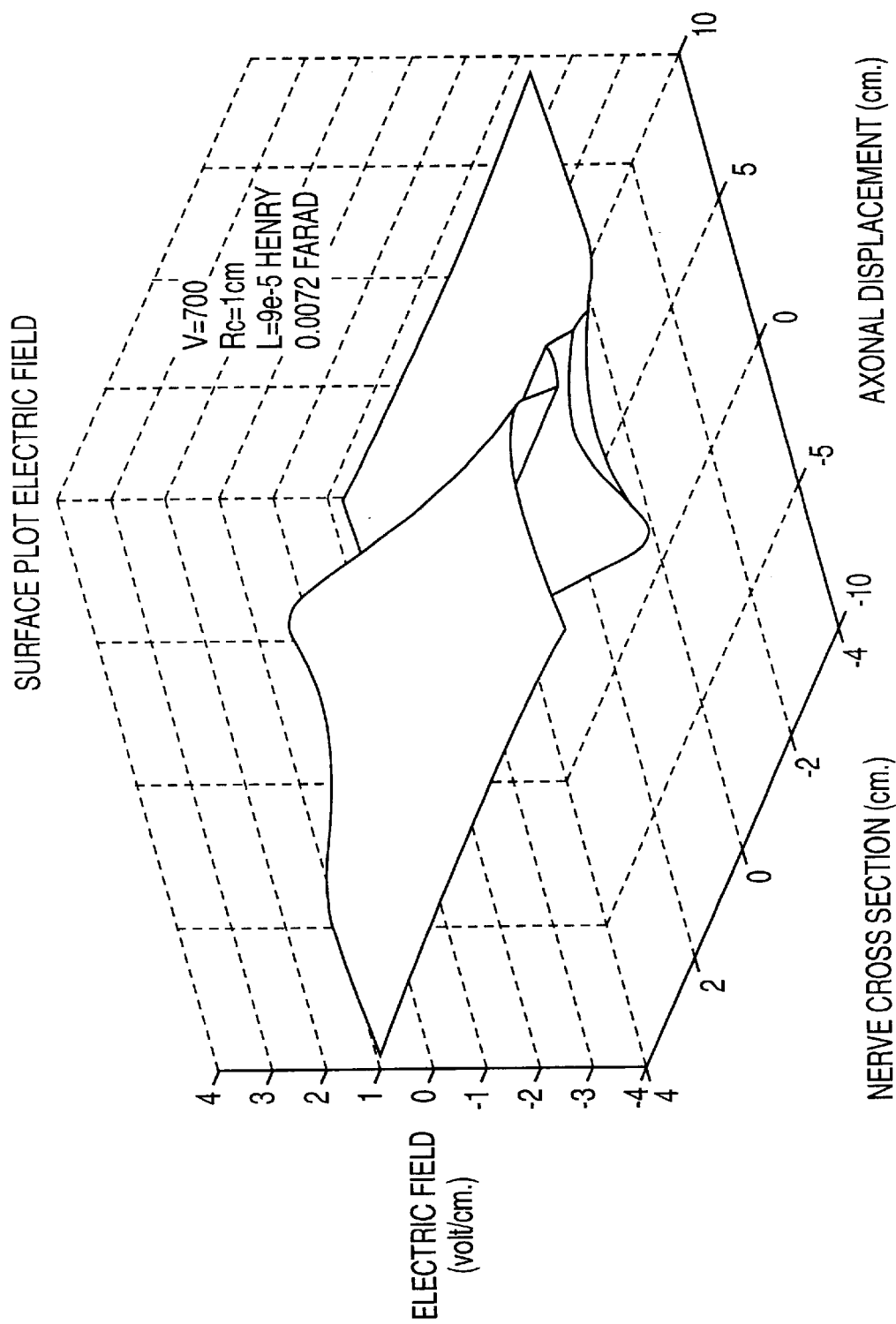
FIG. 4a illustrates the calculated electric field along a length of axon.
Figure 4B:
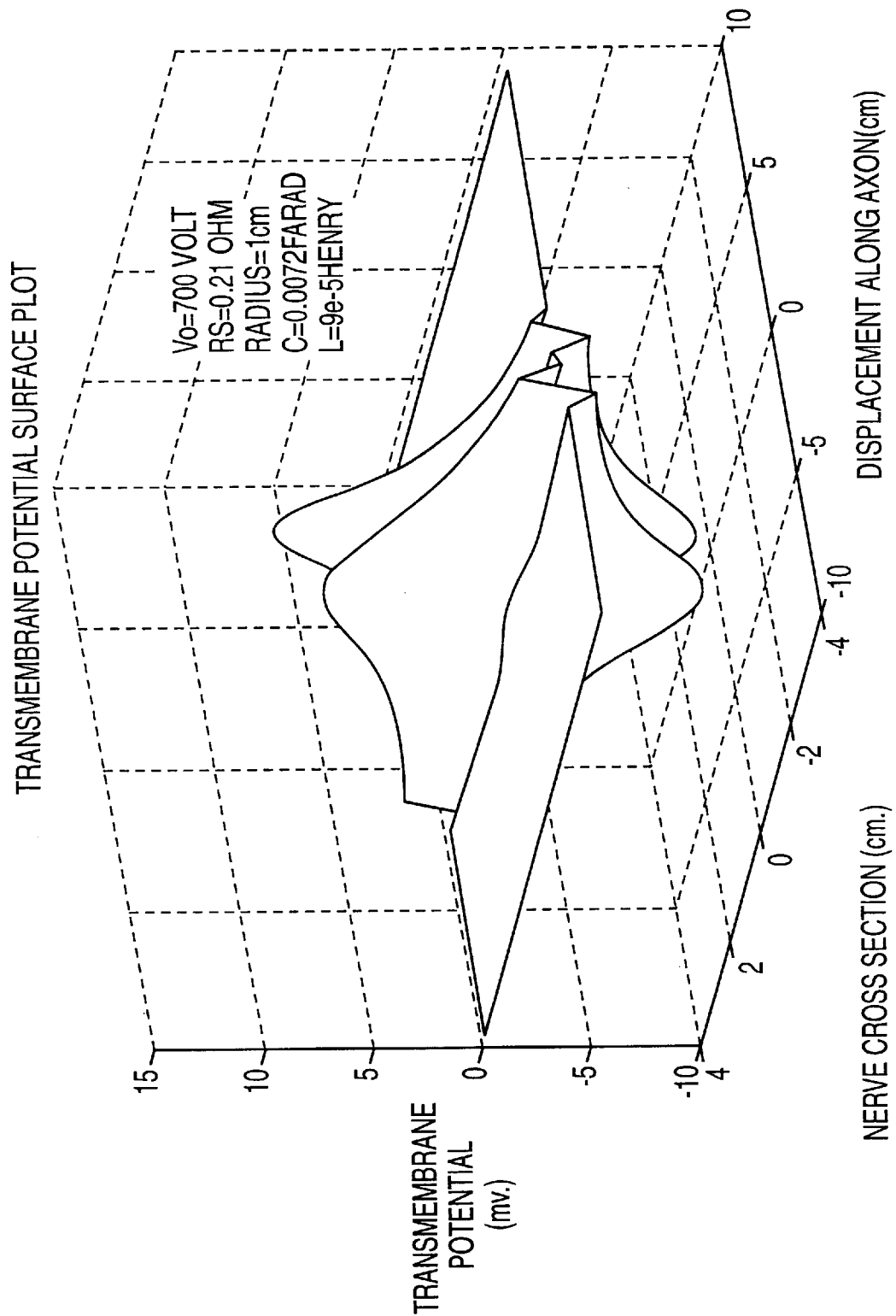
FIG. 4b illustrates the calculated externally induced transmembrane potential along a length of axon using the computer program.

FIGS. 4a and 4b show the results of the calculation of induced electric field and externally induced transmembrane potential, respectively, along the length of the axon using the preceding coil and circuit values. Note that this is the externally induced transmembrane potential induced by the coil. The net transmembrane potential would be equal to the induced transmembrane potential plus the resting potential of the neuron (e.g.−70).

The time is 60 microseconds from the application of 100 volts dc across the circuit. FIG. 4a shows a surface plot of the induced electrical field in neuronal tissue in a plane 3 cm below the coil. The x and y axes represent all points in that plane. The vertical z axis represents the electric field strength in FIG. 4a and the externally induced transmembrane potential (millivolts) in FIG. 4b.

From examination of the graph in FIG. 4a, it can be seen that there is a maxima and a minima in the electric field. Similarly there are multiple maxima and minima in externally induced transmembrane potential as shown in FIG. 4b. The minima correspond to hyperpolarized points. To block propagation of neural impulses these points have to have an induced transmembrane potential more negative than −30 mv. In that case the net transmembrane potential at these points will be greater than −100 mv and thus cannot be depolarized by an advancing action potential.

Among the maxima in the graph there are points with an induced transmembrane potential of greater than 10 mv. Thus the net transmembrane potential at these points will be greater than −60 mv and thus can initiate depolarization and an axonal impulse.

FIGS. 4c–4g show the graphs of the externally induced transmembrane potential across a specific cross section of the nerve bundle. These graphs correspond to the coil used for FIGS. 4a and 4b. FIGS. 4c–4g would correspond to a specific y value (position along the axon). The vertical axis shows the externally induced transmembrane potential at each point along a cross section of a nerve bundle. The calculation was done for a cross section from x=−4 to +4 cm.

Obviously there are no nerve bundles with such a large diameter. However the graph allows one to see how the externally induced transmembrane potential is affected by the positions of a nerve bundle with respect of the overlying coil. The electrical parameters for the coil circuit are those given in Example 1. The data presented in these graphs is simply a subset of the data shown in FIGS. 4a and 4b.

Figure 4C:
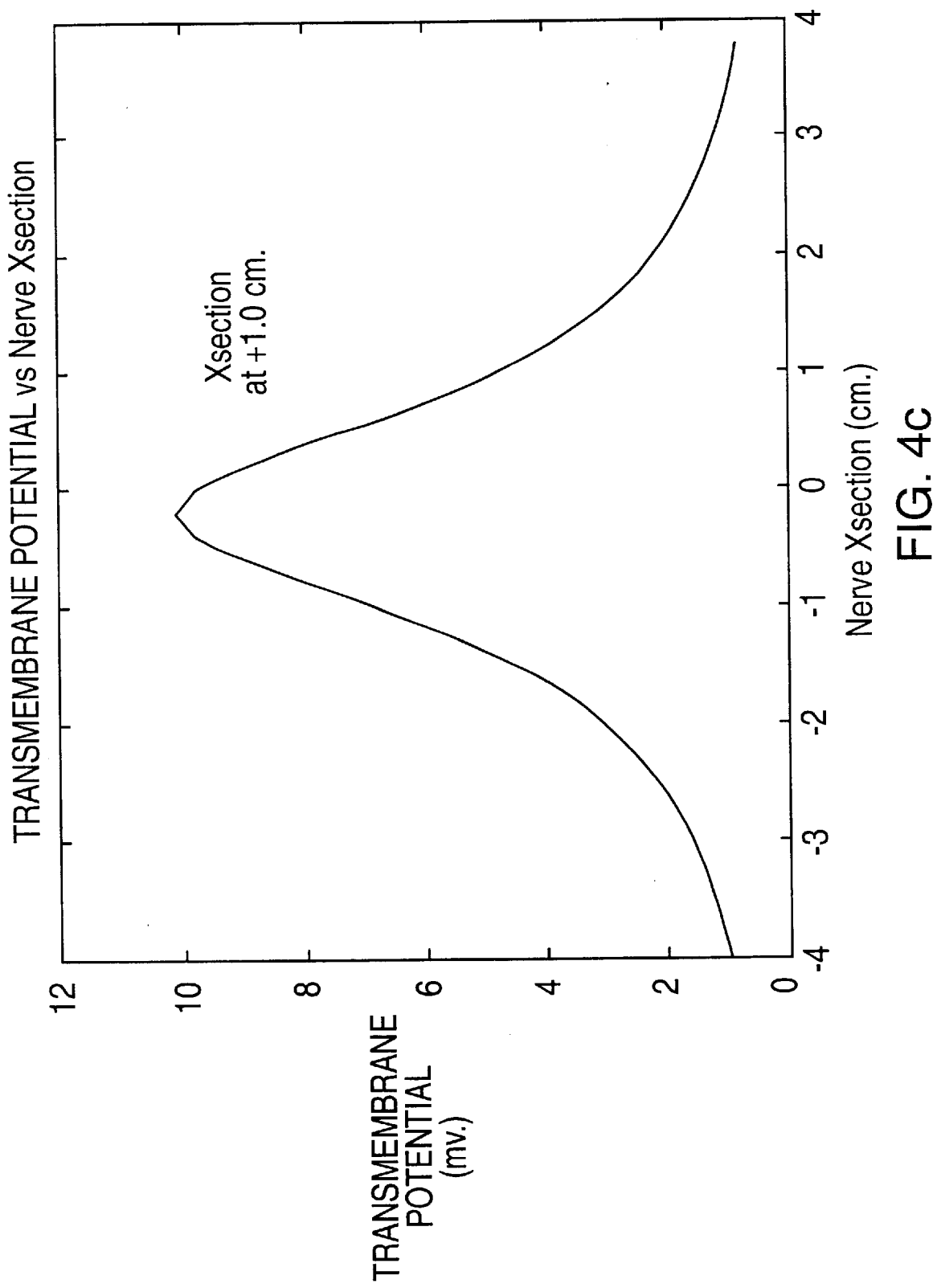
Figure 4D:
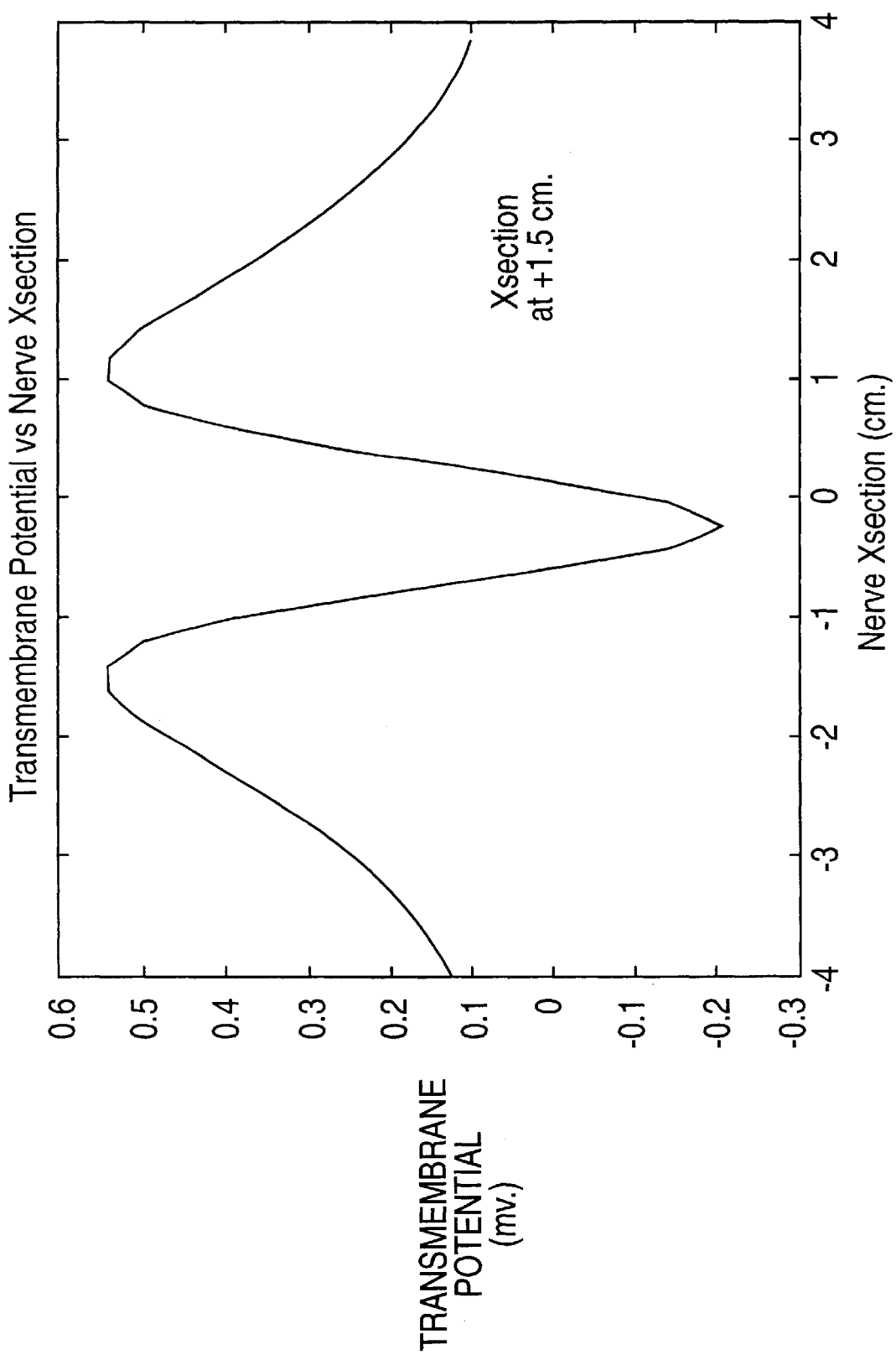
Figure 4E:
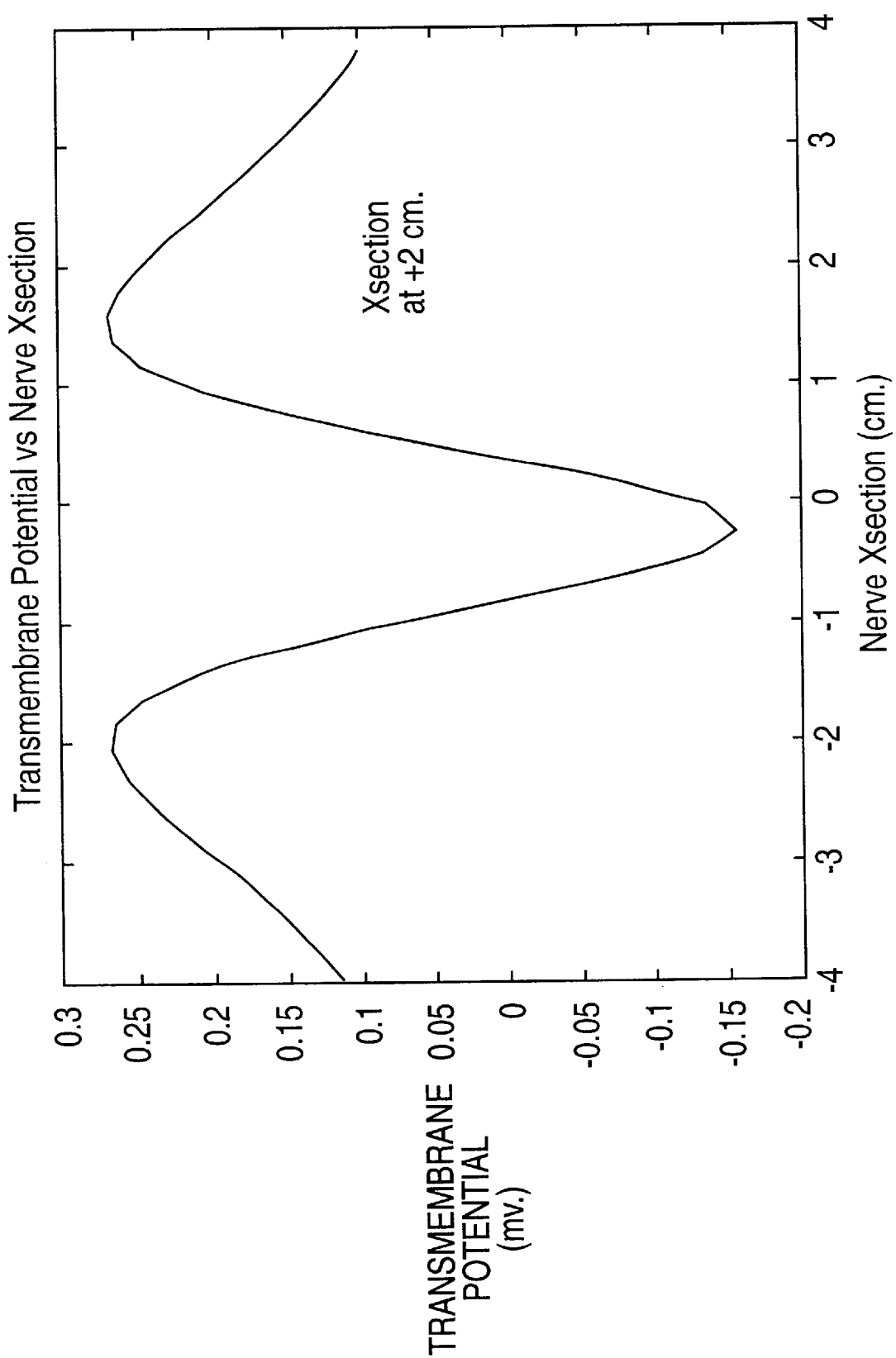

FIG. 4c shows the externally induced transmembrane potential at the nerve bundle cross section which is +1.0 cm. from the center of the coil. At this point it can be seen that there is a sharply delineated zone where the externally induced transmembrane potential rises to a value of 10.2 mv. This is just above the value necessary to cause depolarization. What is even more important is the singularity of the maxima and the linearity of the data around this point.

These two features provide for the stimulation of only a small zone within a nerve bundle. Ideally, a single axon within the bundle is stimulated. One of the critical objects of this invention is the ability to cause focal axonal stimulation.

That is because different axonal fibers within a nerve bundle correspond to different end organ receptors and thus would be carrying different neural impulses to the brain. In order to accomplish this it is necessary to have a means of creating a focal change in the externally induced transmembrane potential that would not affect adjacent axonal fibers.

Given that the maxima in FIG. 4c is a single point it is possible to make the zone of stimulation as narrow as desired. This can be proven on the basis of the theory in mathematical analysis called the continuity theory. This states that for a curve for any two chosen points (such as the points where the externally induced transmembrane potential equals 9.5 and top of the curve where it is 10.2 mv), all intermediate values on the curve exist.

In fact, it is possible to make minor changes to the voltage so that the maxima can take on values as close to 10.0 as desired. As the maxima get closer and closer to 10 mv, the range of x values (along the cross section of the nerve) for which the externally induced transmembrane potential is greater than 10 mV., can be made as small as desired. This is a result of the aforementioned continuity theory. Thus, it is literally possible to make the zone of axonal stimulation as narrow as desired. Thus, the present invention has the complete ability to focus the stimulation and stimulate only one axon if desired.

In addition, it will be noted that at all cross sectional segments to the right, (more positive than the current one (x=1.0 cm) have no areas of critical hyperpolarization (<−40) or depolarization (>10). This can be seen by observing FIGS. 4d (x=1.5 cm), 4e (x=2 cm), 4f (2.5 cm), and 4g (3.0 cm). For the purpose of sensory stimulation, the coil will be oriented so that the region to the right of the coil (x>0) is lying on the proximal side of the neuron (closer to the brain than the coil).

Thus, the present invention provides a means of selectively stimulating a tiny (axonal) segment of a nerve bundle and then propagating that signal. Because of the absence of areas of critical hyperpolarization and depolarization to the right of the signal origin, it will always remain as focused desired.

As noted before, a conventional preliminary study has to be carried out so as to pinpoint which axon to stimulate for a specific sensory perception. Then this axon is stimulated in accordance with the present invention.

EXAMPLE 2

A different set of parameters for the RLC circuit and coil will enable production of sufficient transmembrane voltage to produce blockade of a neural impulse. There are different possible combinations of circuit and coil parameters which will satisfy the required transmembrane voltage criteria. The following example illustrates one set of conditions which produces the desired effect. One set of values of circuit and coil which yield sufficient externally induced transmembrane potentials are:

Rc=radius of coil=1 cm,
Rw=radius of wire=1 mm,
Resistance R=0.16 ohms,
Capacitance C=0.0007 Farad,
Inductance of coil=L=9e-5 Henry,
Voltage=Vo=1700 volts, and
z0=height is coil above axon=3 cm.

If a hyperpolarized region is more distal, with respect to the direction of propagation of the action potential, the impulse should be blocked from traveling in the retrograde direction. The retrograde direction would be along the axon towards the sensory end organ. Blocking (in more dense neuronal tissue such as brain) can help to ensure a focused neuronal stimulation.

Figure 4H:
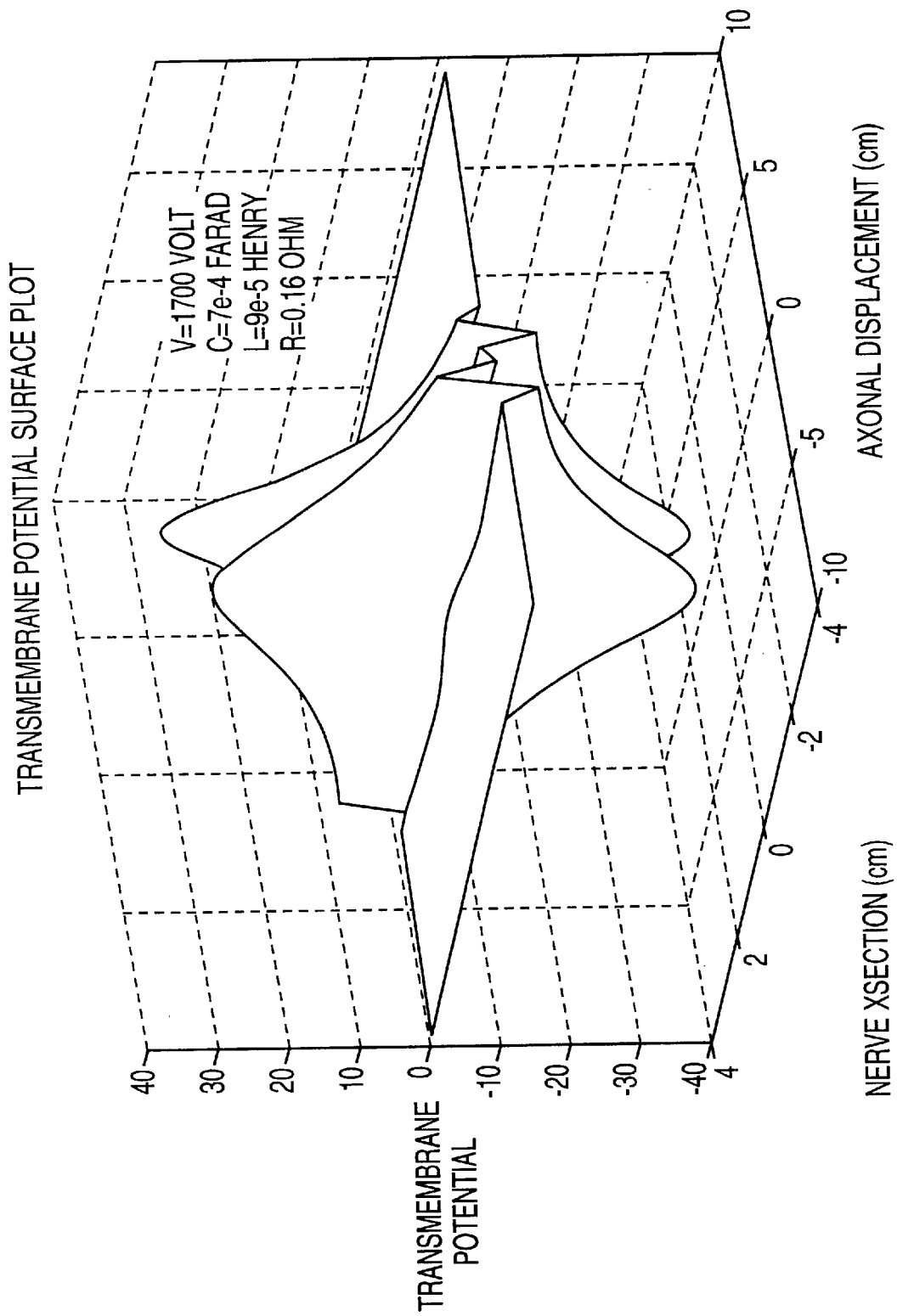
FIG. 4h illustrates the calculated externally induced transmembrane potential along a length of axon using the computer program with a different set electrical circuit parameters than FIG. 4b.

The present invention provides for selective stimulation of axonal fibers within a nerve bundle while surrounding axonal fibers are blocked. Blocking can also achieve another beneficial effect. That is neuronal anesthesia and analgesia for pain control for surgical and non-surgical patients. FIG. 4h shows a surface plot of the transmembrane potential over the neuronal plane.

FIG. 4i shows the externally induced transmembrane potential versus nerve cross-section plot in the same format as before. However, in this case, the coil's electrical parameters are different. This neuronal cross-section was taken −1.5 cm from the center of the coil.

Figure 4J:
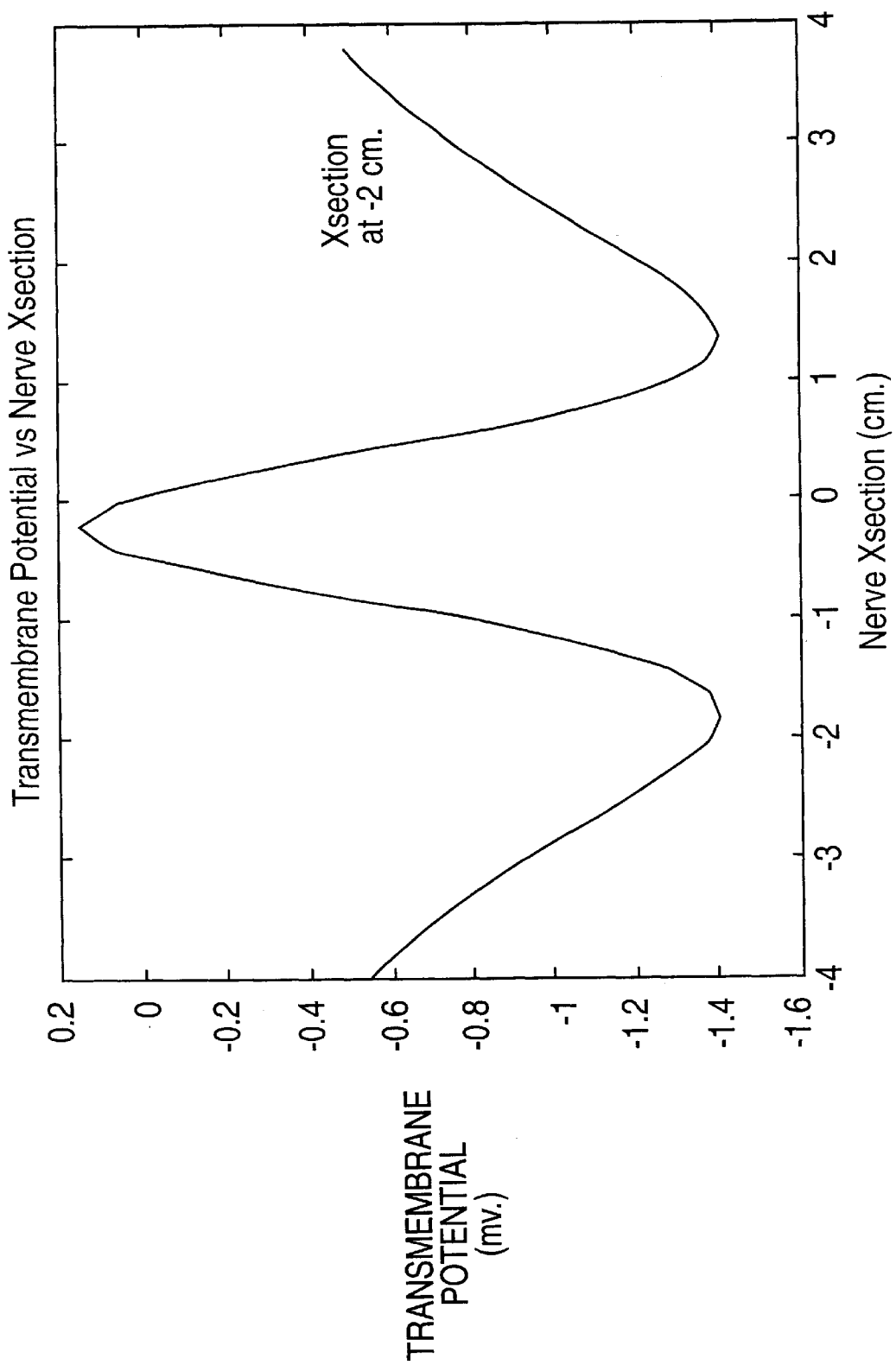
Figure 4K:
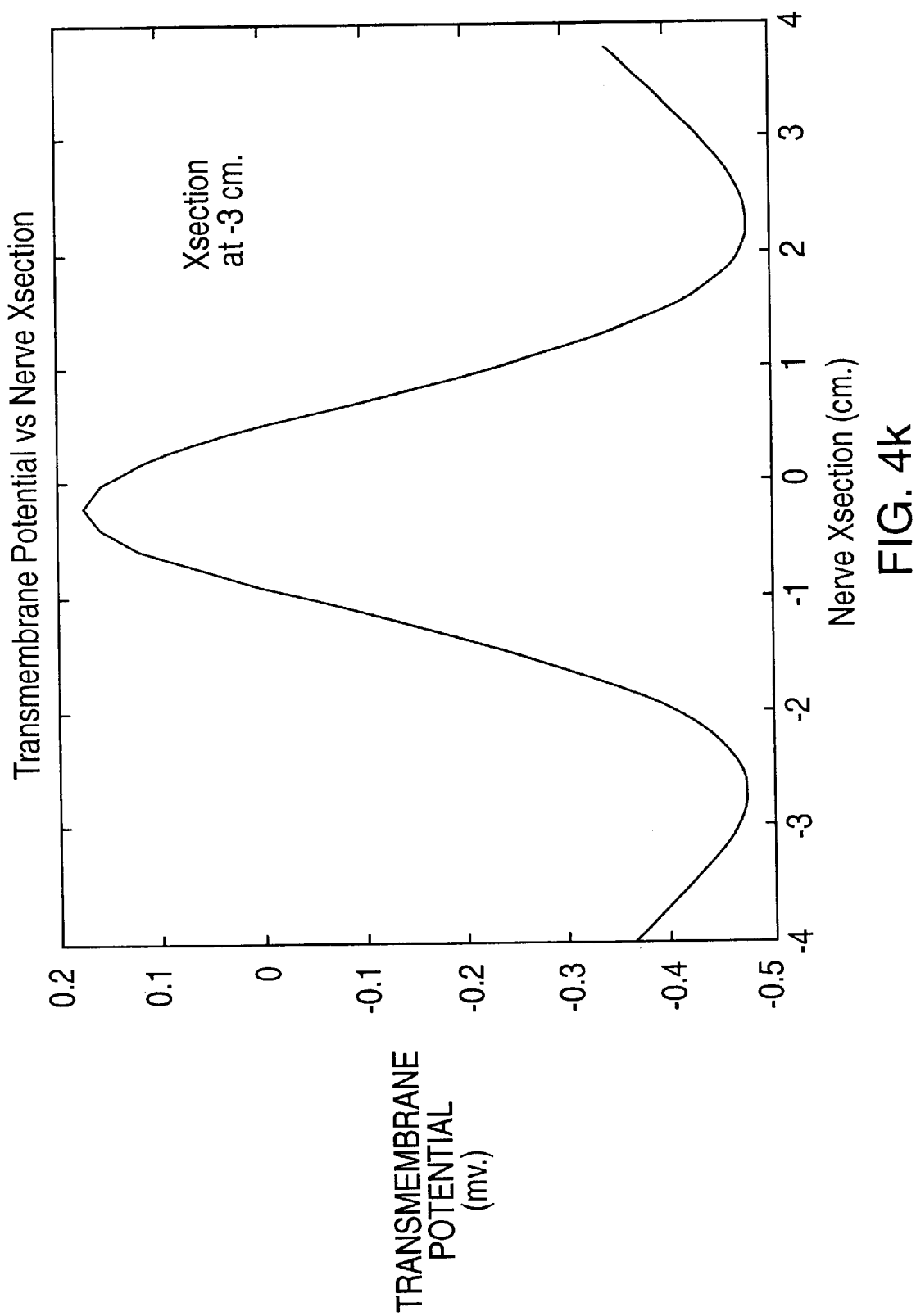

It can be seen from examining FIG. 4h that the neuronal tissue that lay between −1 cm and 1 cm (on the cross-section) has a externally induced transmembrane potential more negative than −30 mv. This would be sufficiently hyperpolarized to prevent the propagation of any nerve impulses. This is an example of how to block all neural impulses from passing a given point on the nerve bundle. FIGS. 4j and 4k show the externally induced transmembrane potentials at −2 and −3 cm, respectively, from the axis of the coil.

To have the selective axonal stimulation generated in the cross-section shown in FIG. 4c, and only have the signal propagate in the antegrade direction, that is towards the brain, the first coil (corresponding to FIG. 4c) with the target neuronal tissue displaced 1.0 cm from the center of the coil, the second coil corresponding to the graph shown in FIGS. 4i, 4j and 4k, it was shown that at −1.5 cm from the center of the coil, there is a zone of hyperpolarization from −1 to 1 cm cross-section that was adequate to block a neuronal impulse.

Referring back to FIGS. 4j and 4k, it can be seen that the imposed externally induced transmembrane potential in the zone from −1 to 1 cm (cross-section) continues to decrease until it is only −1.2 to 0.2 mv at −2 cm and −0.3 to 0.2 mv at −3 cm from the coil's center. Now displace the center of the blocking coil >3 cm more distal (with respect to the brain) from the center of the stimulating coil. Then the externally induced transmembrane potential from the blocking coil at that point (−3 cm) is −0.2 mv will be superimposed on the externally induced transmembrane potential shown in FIG. 4c. Thus, there will be a very tiny drop in the stimulating potential.

This can easily be overcome by increasing the voltage in the stimulating coil to 750 volt. Then the net transmembrane potential at the triggering point (1 cm to the right of the stimulating coil) will then be >10.0 mv and thus adequate to stimulate the antegrade neuronal impulse while at the same time it will be blocked from traveling in the retrograde direction by the second blocking coil.

But what about the zone on the positive (>0) side from the blocking coil. This is the point 1 cm to the right of the center of the blocking coil. There is a positive transmembrane potential sufficient to cause a depolarization that would propagate to the sensory organ. However we can keep the blocking effect of the coil, yet eliminate the propagation towards the sensory organ by placing the center of the coil so that it is 0.5 cm distal to the sensory organ. Thus, the blocking effect will occur proximal to the sensory end organ but the stimulation zone will be distal to the sensory organ and thus have no nerve to stimulate.

It will be understood from the prior description that if the blocking coil is used alone, it can easily block an antegrade neural signal traveling from a point more distal >−1.5 cm with respect to the center of the blocking coil towards the brain. That is because those more distal impulses will encounter the same hyperpolarized area at −1.5 cm. The only difference is that the impulse is traveling in the opposite direction.

Therefore, a method of preventing retrograde conduction of an impulse and a method to produce sensory analgesia and anesthesia is disclosed. Furthermore, the blocking can be used to prevent motor nerve conduction for the purpose of treating a problem such as peripheral motor spasticity.

The device disclosed in this application can also be used to induce general or central nervous system anesthesia. Precise areas of the brain are targeted. More specifically, regions of hyperpolarization and/or depolarization are induced in one or more areas of the brain in order to prevent conduction of somatosensory pain.

In addition, creating areas of depolarization or hyperpolarization in the brain prevent altered states of consciousness and unconsciousness where the patient is insensitive to the pain afferent input and completely unaware of the operation being performed. In order to do this, the specific areas which mediate pain and consciousness is targeted.

Although not all the anatomic areas and interconnections which control pain and consciousness have been identified, much is known about them. For example, it is known that third order neurons are located in the thalamus and send fibers to somatosensory areas I and II in the post central gyrus of the parietal cortex and the superior wall of the sylvian fissure, respectively.

Perception and discrete localization of pain take place in these cortical areas. While most neurons from the lateral thalamic nuclei project to the primary somatosensory cortex, those from the intralaminar and medial nuclei project to the anterior cingulate gyrus and likely mediate the suffering and emotional components of pain.

In their paper entitled: "Inhalational Anaesthetics Exhibit Pathway Specific and Differential Actions on Hippocampal Synaptic Responses In Vitro" (Br. J. Anaesth. (1988), 60,680–691) MacIver M B and Roth S B focused their attention on the ability of inhalational anesthetics to affect excitability of hippocampal synaptic junctions, which is believed to be involved in both pain and level of consciousness.

In an article entitled: General Anesthetics Hyperpolarize Neurons in the Vertebrate Central Nervous System" (Science 1982;217: 1055–1057) Authors Nicoll R A and Madison D V discuss the correlation between level of anesthesia and degree of hyperpolarization of neurons in the spinal cord and hippocampus. In a paper entitled: "Anesthetics and Excitatory/Inhibitory Responses of Midbrain Reticular Neurons" (Anesthesiology 61:151–155, 1984) authors Shimoji K, Fujioka H, et al. concluded that suppression of excitatory neurons in the midbrain reticular formation was likely to be a general feature of anesthetic state.

In the paper entitled: "Isoflurane Hyperpolarizes Neurones in Rat and Human Cerebral Cortex (Acta Physiol Scand 1987;130: 679–685) Berg-Johnsen J and Langmoen I A showed that isoflurane's effect on neurones from the hippocampal cortex and human neocortex was to hyperpolarize the neurons and thereby interfere with conduction.

Thus, hyperpolarization and/or depolarization of select sites in the central nervous system can be used to produce unconsciousness and anesthesia. Thus, the device disclosed can be used to produce hyperpolarization and/or depolarization in these areas in the brain to produce the same anesthesia and unconsciousness which is currently produced only through the direct exposure of these areas of the brain to general anesthetics.

Figure 5:
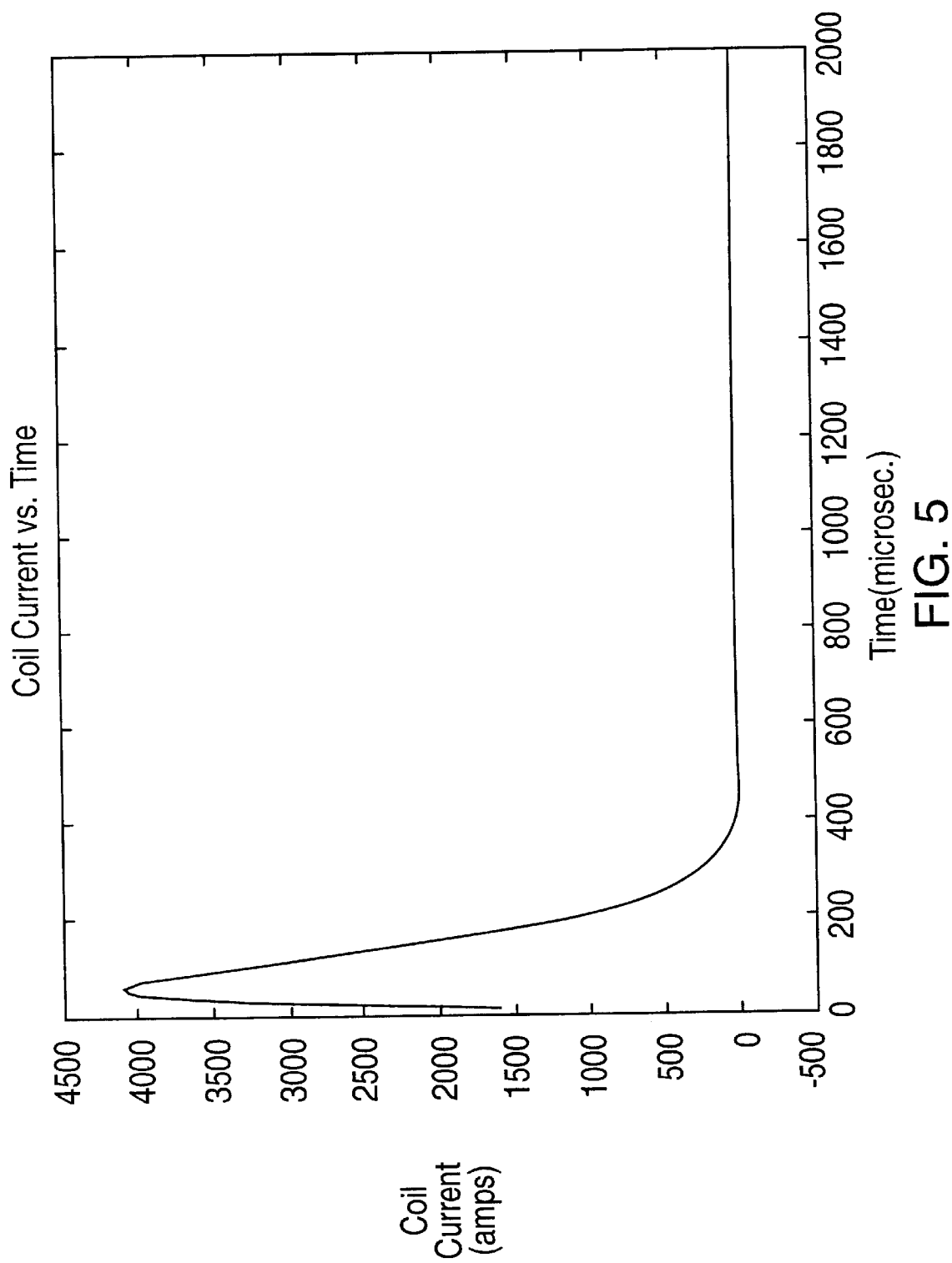
FIG. 5 illustrates current versus time for a coil used in accordance with the present invention.

FIG. 5 shows the results of the calculation of the current as a function of time. The current is expressed in units of amps and time is expressed in units of microsecs.

Referring back to Equation 10, it can be seen that the electric field is directly proportional to rate of current change with respect to time (dI/dt). In order to maintain an adequate transmembrane potential, the electric field strength and, thus, the time derivative of current must be sufficiently large.

Using the computer program shown in FIG. 3, the requisite time derivative of the current in order to maintain the externally induced transmembrane potentials given in Examples 1 and 2 can be calculated. For the parameters given in Example 1, the requisite minimum time derivative of the current is 3.62 $10^7$ amps/sec. Furthermore, an adequate current time derivative only occurs during the first 60 microseconds after discharge of the given RLC circuit.

Referring back to FIG. 5, it can be seen that this time interval corresponds to the portion of the current versus time curve where there is a rapid rise in current from 0 amps to 5827.6 amps over a 60 microsecond interval. Therefore, in order to maintain the proscribed transmembrane potential, it is necessary to have an electrical circuit which can maintain this rapid rise of current change through the magnetic coil at all times. In order to accomplish this, two components are needed.

The first is a high voltage DC generator which can produce high voltage DC pulses at a rapid rate. This type of circuit is well known to those experienced in the art of electronics. There are many commercial firms which manufacture such high voltage supplies. One such company is Huettinger Electronic, Inc, (111 Hyde Road, Framington, Conn. 06032, USA). Many other circuits can also be used to produce high frequency, high voltage DC pulses. One such circuit is shown in FIG. 9.

Figure 9B:
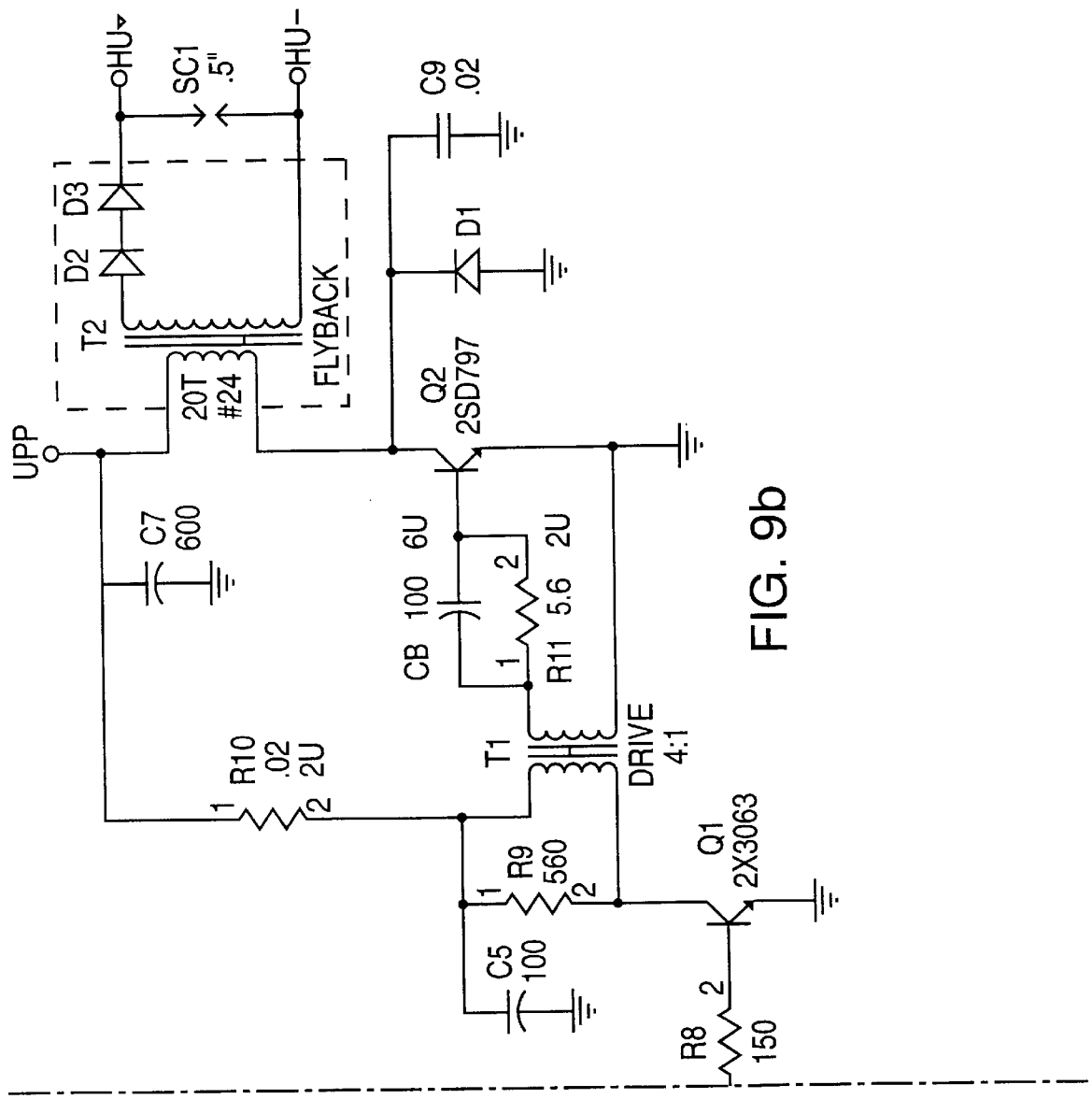

As shown in FIG. 9, horizontal drive transformer (T1) was from small B/W monitor, flyback transformer (T2) was from MacIntosh Plus computer monitor, original primary windings were removed, component values are not critical, output may exceed 25,000 V at certain frequencies with 24 V power—could destroy flyback. Sparkgap provides more protection. Input power was current limited to about 5 A. Good heat sink is important on Q2 for continuous operation.

Regardless of how fast the high voltage generator can pulse a RLC circuit, there will be a discontinuity in the current gradient and thus the externally induced transmembrane potential. That is because the current flow in the circuit must drop back down to zero so that there can be another steep rise in current which is necessary to generate the proper externally induced transmembrane potential.

In order to prevent discontinuity in the externally induced transmembrane potential, this invention provides for two separate RLC circuits with identical values for resistance, inductance, capacitance and initial voltage. Both circuits are powered by high frequency high voltage DC pulses. The two coils are proximate to each other so that they produce the same spatial and temporal distribution of electric fields for a given coil current.

Figure 6:
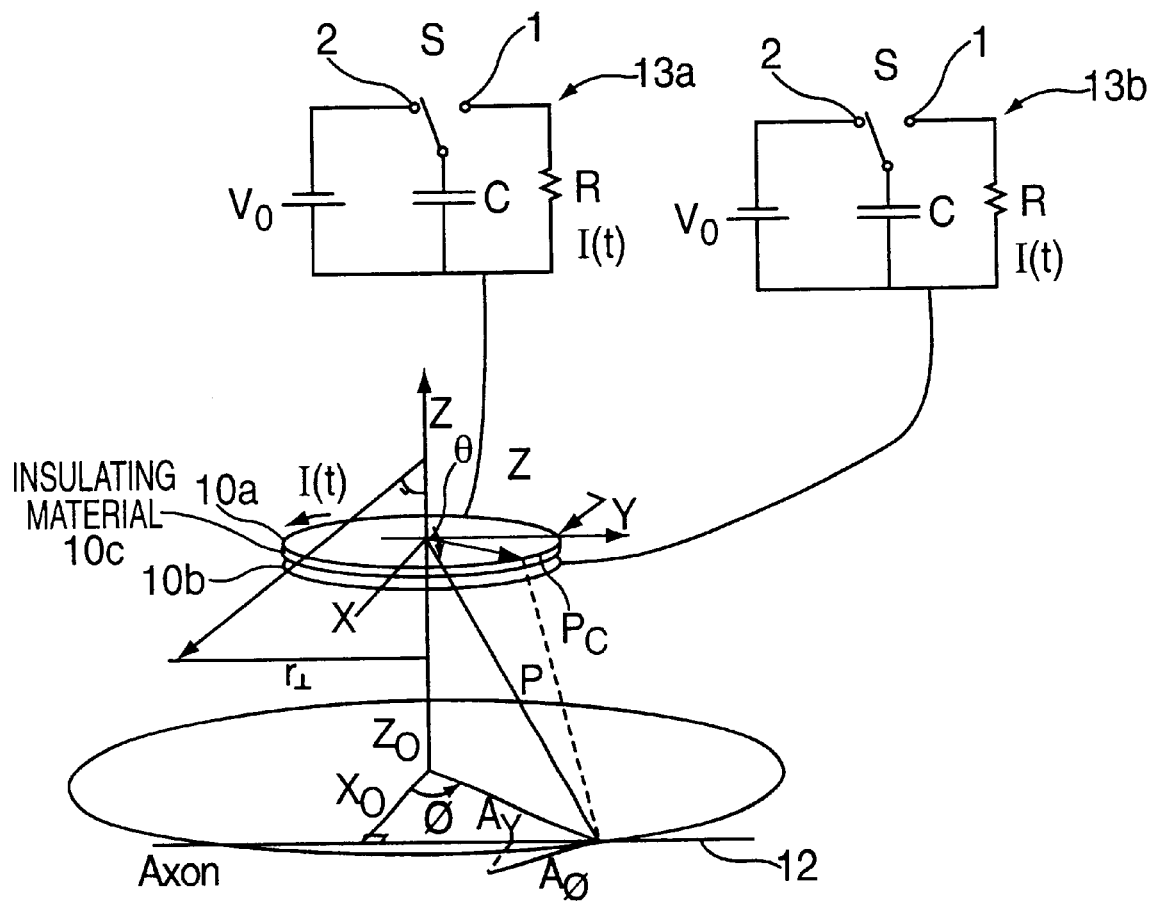
FIG. 6 illustrates two proximate coils used to maintain the magnetic flux.

FIG. 6 illustrates such an arrangement. As shown, one coil 10a is positioned directly on top of the other coil 10b with insulating material 10c positioned between the two to prevent direct electrical contact. For the purpose of the rest of this document, the conglomerate of the two proximate coils will be referred to by the number 10.

In addition to the proximate coils 10, there is a high speed discharge circuit which will short circuit the capacitor in the RLC circuit 13a and 13b and, thus, bring the circuit current down to zero almost instantaneously. The two circuits 13a and 13b are timed so that the second circuit is pulsed with a DC discharge 50 microseconds after the first circuit was pulsed. Ten microseconds later, the first circuit is short circuited so that the current in the coil drops to zero.

Fifty microseconds later, the first circuit receives its next DC pulse. Ten microseconds later the second circuit is short circuited. This cycle is repeated continuously so that there is always one coil with a large enough value of dI/dt to produce the requisite externally induced transmembrane potential in a continuous fashion.

There is another means of blocking action potentials. That is through the creation of an extracellular potential gradient which opposes the flow of the excitatory action current ahead of the depolarized membrane. It has been reported that the imposition of a blocking potential directly ahead of an oncoming action potential can block the propagation of that action Potential (Van Den Honert C and Mortimer T J, A Technique for Collision block of Peripheral: Single Stimulus Analysis, IEEE Transaction on Biomedical Engineering, Vol. BME-28,No. 5, May 1981).

In the past, this potential has been achieved by the direct application of a tripolar cuff around the target nerve. Using this technique two anode electrodes surround a cathode thereby creating two extracellular currents, one from each anode to the central cathode.

Figure 7A:
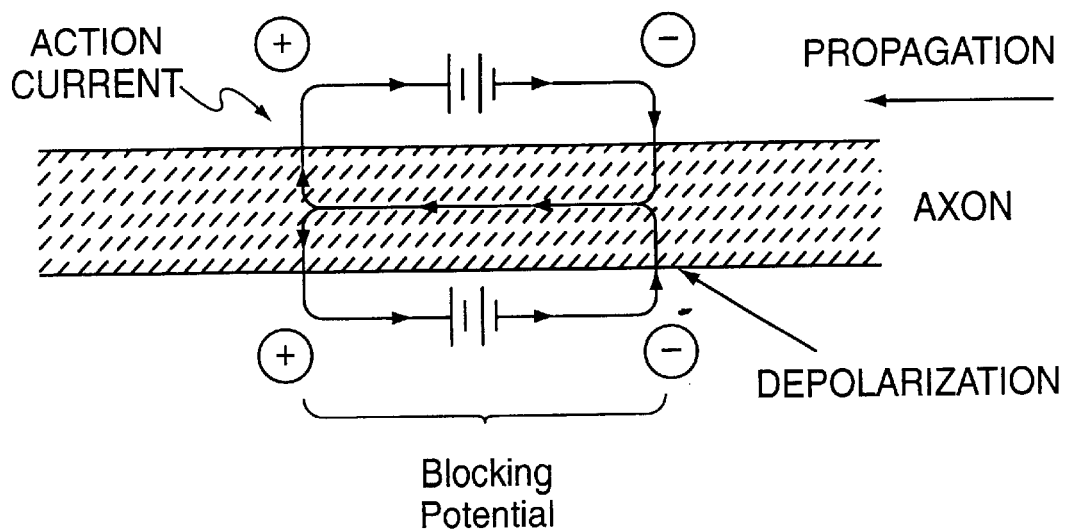
FIGS. 7a–7c illustrate the tripolar cuff and the blocking potential.
Figure 7B:
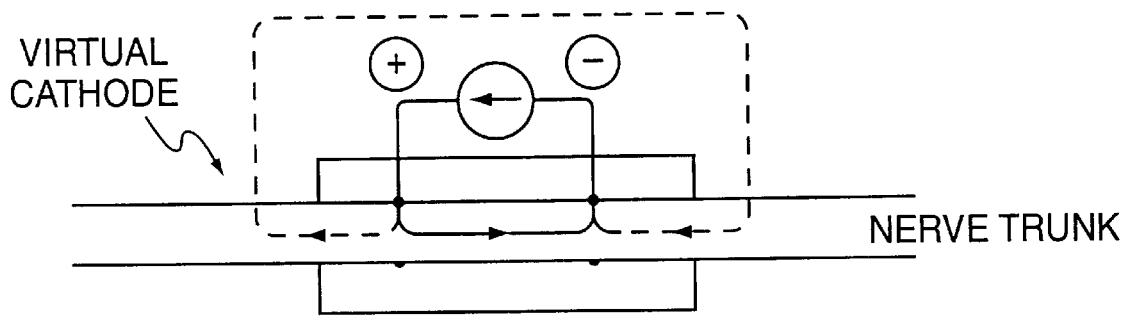
Figure 7C:
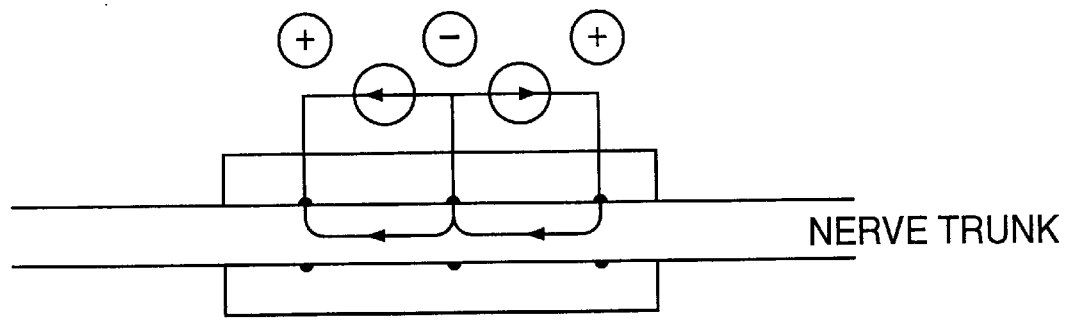

FIGS. 7a–7c illustrate the tripolar cuff and the blocking potential.

FIG. 7a is a schematic representation of action current loops established by a propagating action potential. Extracellular current establishes a blocking potential which opposes the flow of the action currents.

FIG. 7b shows an insulated bipolar electrode, external leakage current gives rise to a virtual cathode outside the insulator.

FIG. 7c illustrates a tripolar electrode configuration containing the current flow within the insulator.

Using the coil described in FIG. 6 with a current labeled as I(t), the externally induced transmembrane potential pattern shown in FIG. 4b can be produced in a time invariant manner.

Looking at the pattern, moving along the axon from left to right, there is a region of hyperpolarization followed by a region of depolarization. If the current through the coils happened to be reversed, I'(t), then the location of the hyperpolarized region and the depolarized region would be reversed.

If the two coil groups, with the opposite current flow, are not superimposed but are separated so that their centers are 5 cm apart, then the hyperpolarized zones produced by the two sets of coils will be adjacent to each other. This hyperpolarized region will be surrounded by two depolarized regions. Thus, a virtual tripolar cuff is created. In the same way as with the tripolar cuff, this virtual tripolar will produce a blocking potential which opposes the flow of the action current which precedes the action potential in the extracellular space.

As was mentioned earlier, by blocking the action current, the propagation of the action potential is stopped. This provides for a second way of producing neural blockade which can be used in the sensory stimulation embodiment to prevent retrograde conduction. Additionally, it can be used alone to block antegrade sensory nerve conduction, thereby creating anesthesia and analgesia using electromagnetic fields.

FIG. 8 shows a means for positioning coil 10 in the proximity of the targeted axon 12. Coil 10 is suspended over a targeted axon 12 of patient's arm 14. Arm 14 is fixed in position on positioning board 16. Positioning board 16 permits precise positioning of XY positioner 18. XY positioner 18 has two servomotors which allow positioner 18 to a specified location on board 16. Affixed to positioner 18 is support pole 20. At the top of support pole 20 is servomotor driven coil positioner 22. XY positioner 18 and coil positioner 22 provides three degrees of freedom. The first is in the Z direction. Coil positioner 22 moves coil 10 towards or away from axon 12 in the Z or vertical plane. The other two degrees of freedom are provided by XY positioner 18 and the X and Y axes on positioning board 16. These axes, X, Y and Z correspond to the x, y, and z axes shown in FIG. 4. The overall movement of XY positioner 18 and coil positioner 22 are controlled via computer, associated circuitry and power source 24 via wire 26. The circuitry necessary to produce a varying magnetic field in coil 10 is conventional.

What is claimed is:

1. A method for sensory stimulation or sensory blockage in a patient comprising the steps of:
    creating a time varying magnetic field with a plurality of magnetic flux generators each positioned completely external to said patient and oriented to the same neural tissue, said time varying magnetic field resulting in an electric field which creates one or more regions of hyperpolarization or depolarization along said neural tissue, for as long as required to produce a continuous blockage or stimulation of said neural tissue, said regions of depolarization causing the propagation of a sensor neural impulse and said regions of hyperpolarization being of sufficient magnitude to block the propagation of nerve impulses in said neural tissue preventing retrograde sensory conduction or producing sensory anesthesia.

2. The method of claim 1 wherein each of said magnetic flux generators has a coil which can produce a time varying magnetic field.

3. The method of claim 2 wherein said coil is circular in shape and has about 7 to about 10 turns, and the coil has a diameter of about 3 to about 7 cm.

4. The method of claim 2 wherein the coil has a resistance (R) of about 0.1 to about 0.5 ohms and an inductance (L) of about 10 to about 90 microhenrie.

5. The method of claim 1 wherein each of said magnetic flux generators consist of a resistor, capacitor and inductor in series.

6. The method of claim 5 wherein said capacitor is discharged through said resistor and inductor so as to form a time varying magnetic field which in turn creates said electric field.

7. The method of claim 1 wherein a time varying current passes through each of said magnetic flux generators and said time varying current increases from 0 to about 6000 amps in 60 microseconds.

8. A system consisting of
    a plurality of magnetic flux generators, said magnetic flux generators being configured so that the effect is to produce continuous blockade of one or more than on nerves.

9. The system of claim 8 wherein said magnetic flux generators produce an electrical field which creates a triphasic potential within the axon, said triphasic potential consisting of a virtual cathode surrounded by a virtual anode on either side o said virtual cathode.

10. The system of claim 8 wherein each of said magnetic flux generators has a coil of wire organized in such a way to allow production of a strong focused electrical field at one or more interior points in the brain while sparing all other points in the brain.

11. The system of claim 8 wherein each of said magnetic flux generator has a coil which is positioned with a three dimensional electromechanically controlled positioning system.

12. The system of claim 8 wherein each of said magnetic flux generators has a coil affixed to the body part containing a target nerve thus providing for continuous acute or chronic pain control.

* * * * *